(12) United States Patent
Arstad et al.

(10) Patent No.: US 8,506,932 B2
(45) Date of Patent: Aug. 13, 2013

(54) TETRACYCLIC INDOLE DERIVATIVES AS IN VIVO IMAGING AGENTS AND HAVING PERIPHERALBENZODIAZEPINE RECEPTOR AFFINITY (PBR)

(75) Inventors: Erik Arstad, London (GB); Ian Wilson, Buckinghamshire (GB); Sajinder Kaur Luthra, London (GB); Frank Brady, London (GB); Bengt Langstrom, Uppsala (SE); Farhad Karimi, Canton, MA (US); Edward George Robins, London (GB); Bo Shan, London (GB)

(73) Assignee: Hammersmith Imanet Limited, London (GB)

( * ) Notice: Subject to any disclaimer, the term of this patent is extended or adjusted under 35 U.S.C. 154(b) by 468 days.

(21) Appl. No.: 12/094,172

(22) PCT Filed: Nov. 20, 2006

(86) PCT No.: PCT/GB2006/004342
§ 371 (c)(1),
(2), (4) Date: Oct. 6, 2008

(87) PCT Pub. No.: WO2007/057705
PCT Pub. Date: May 24, 2007

(65) Prior Publication Data
US 2009/0220420 A1 Sep. 3, 2009

(30) Foreign Application Priority Data

Nov. 18, 2005 (GB) .................................. 0523506.4

(51) Int. Cl.
*A61K 49/00* (2006.01)
(52) U.S. Cl.
USPC ......... 424/9.1; 424/1.11; 424/1.65; 424/1.81; 424/1.85; 424/1.89
(58) Field of Classification Search
USPC .................... 424/1.11, 1.65, 1.81, 1.85, 1.89, 424/9.1, 9.2, 9.3, 9.4, 9.5, 9.6, 9.7, 9.8; 548/400; 549/1
See application file for complete search history.

(56) References Cited

U.S. PATENT DOCUMENTS

| | | | |
|---|---|---|---|
| 6,281,355 B1 * | 8/2001 | Nakazato et al. | 544/14 |
| 6,451,795 B1 | 9/2002 | Marguet et al. | |
| 6,870,069 B2 | 3/2005 | Suzuki et al. | |

FOREIGN PATENT DOCUMENTS

| | | |
|---|---|---|
| EP | 1048651 | 5/2003 |
| FR | 2788776 | 7/2000 |
| JP | 07165721 | 6/1995 |
| WO | 99/51594 | 10/1999 |

OTHER PUBLICATIONS

Okubo, et.al. "Design, synthesis, and structure-activity relationships of novel tetracyclic compounds as peripheral benzodiazepine receptor ligands" Bioorganic & Medicinal Chemistry, vol. 12, 2004 pp. 3569-3580.
GB0523506.4 Search Report dated Mar. 23, 2006.
PCT/GB2006/004342 Int'l Search Report/Written Opinion dated Feb. 6, 2007.

\* cited by examiner

*Primary Examiner* — D L Jones
(74) *Attorney, Agent, or Firm* — Robert F. Chisholm

(57) ABSTRACT

The present invention provides novel tetracyclic indole compounds of Formula (I) either as in vivo imaging agents or as therapeutic agents. A method for the preparation of the in vivo imaging agent compound is also provided by the invention, as well as a precursor for use in said method. Pharmaceutical compositions comprising the compounds of the invention are additionally provided. Where the pharmaceutical composition comprises a compound suitable for in vivo imaging, a kit is provided for the preparation of the pharmaceutical composition. In a further aspect, use of the compound for in vivo imaging or treatment of conditions associated with PBR is provided.

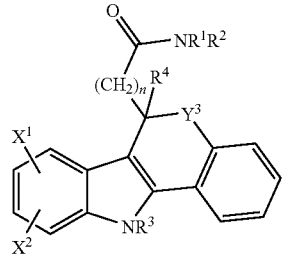

(I)

11 Claims, No Drawings

TETRACYCLIC INDOLE DERIVATIVES AS IN VIVO IMAGING AGENTS AND HAVING PERIPHERALBENZODIAZEPINE RECEPTOR AFFINITY (PBR)

This application is a filing under 35 U.S.C. 371 of international application number PCT/GB2006/004342, filed Nov. 20, 2006, which claims priority to application number 0523506.4 filed Nov. 18, 2005, in Great Britain the entire disclosure of which is hereby incorporated by reference.

TECHNICAL FIELD OF THE INVENTION

The present invention relates to compounds having a high affinity for peripheral benzodiazepine receptors (PBR). Novel compounds are provided which find use in both diagnosis and therapy. In particular, the compounds of the invention are useful for in vivo imaging and for treatment of disease states in which expression of PBR is upregulated.

DESCRIPTION OF RELATED ART

PBR are known to be mainly localised in peripheral tissues and glial cells but their physiological function remains to be clearly elucidated. Subcellularly, PBR are known to localise on the outer mitochondrial membrane. Their presence on the outer membrane of mitochondria indicates a potential role in the modulation of mitochondrial function and in the immune system. It has furthermore been postulated that PBR are involved in cell proliferation, steroidogenesis, calcium flow and cellular respiration. Altered expression of PBR has been observed in a variety of conditions including acute and chronic stress, anxiety, depression, Parkinson's disease, Alzheimer's disease, brain damage, cancer [Gavish et al 1999 Pharm. Rev. 51 p 629], Huntington's disease [Neurosci. Lett. 1998 24(1) pp 53-6], asthma [Gen. Pharmacol. 1997 28(4) pp 495-8], rheumatoid arthritis [Eur. J. Pharmacol. 2002 452(1) pp 111-22], atherosclerosis [J. Nucl. Med. 2004 45 pp 1898-1907] and multiple sclerosis [Banati et al 2000 Brain 123 p 2321]. PBR may also be associated with neuropathic pain, Tsuda et al having observed activated microglia in subjects with neuropathic pain [2005 TINS 28(2) pp 101-7].

Ligands having affinity for PBR are known in the art. A class of indole compounds having affinity for PBR [$IC_{50}$ values for most active compounds of between 0.2 nM and 5.0 nM] is disclosed in U.S. Pat. No. 6,451,795. The patent states that the compounds are useful for the prevention or treatment of peripheral neuropathies and for the treatment of central neurodegenerative diseases. Okubu et al [Bioorganic & Medicinal Chemistry 2004 12 3569-80] describe the design, synthesis and structure of a group of tetracyclic indole compounds having affinity for PBR [$IC_{50}$ values as low as about 0.4 nM]. No particular application of the compounds is discussed. Campiani et al [2002 J. Med. Chem. 45 4276-81] disclose a class of pyrrolobenzoxazepine derivatives that bind to PBR with high affinity [$K_i$ against PK11195 as low as about 0.1 nM].

Positron emission tomography [PET] imaging using the PBR selective ligand, (R)-[$^{11}$C]PK11195 provides a generic indicator of central nervous system (CNS) inflammation. Despite the successful use of (R)-[11C]PK11195, it has its limitations. It is known to have high protein binding, and low specific to non-specific binding. The role of its radiolabelled metabolites is not known and quantification of binding requires complex modelling.

Radioiodinated and radiobrominated isoquinoline carboxamide derivatives having high affinity for PBR are disclosed in JP 07165721 as novel in vivo imaging agents or radiotherapeutic agents for PBR.

There is therefore scope for alternative in vivo imaging agents and therapeutic agents that target PBR.

SUMMARY OF THE INVENTION

The present invention provides novel tetracyclic indole compounds suitable for use either as in vivo imaging agents or as therapeutic agents. A method for the preparation of the in vivo imaging agent compound is also provided by the invention, as well as a precursor for use in said method. Pharmaceutical compositions comprising the compounds of the invention are additionally provided. Where the pharmaceutical composition comprises a compound suitable for in vivo imaging, a kit is provided for the preparation of the pharmaceutical composition. In a further aspect, use of the compound for in vivo imaging or treatment of conditions associated with PBR is provided.

DETAILED DESCRIPTION OF THE INVENTION

In one aspect, the present invention provides a compound of Formula I:

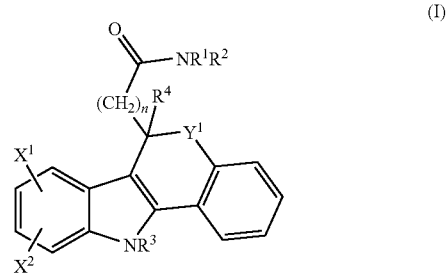

or a salt or solvate thereof, wherein said compound is labelled with an imaging moiety, and wherein:
$X^1$ and $X^1$ are independently selected from hydrogen, halogen, $C_{1-6}$ alkoxy, $C_{1-6}$ alkyl;
$R^1$ and $R^2$ are independently selected from $C_{1-6}$ alkyl, $C_{1-6}$ aminoalkyl, $C_{1-6}$ alkoxyalkyl, $C_{1-6}$ alkoxy, $C_{1-6}$ hydroxyalkyl, a polyethylene glycol (PEG) group, $C_{3-10}$ cycloalkyl, $C_{3-10}$ cycloethers, and $C_{3-10}$ cycloamines;
$R^3$ is the group -A-$R^5$ wherein:
  A is the optional group —$(CH_2)_z$—$R^6$— wherein z=0-6, $R^6$ is a 5- or 6-membered heterocycle having 1-3 heteroatoms selected from N, S and O, and wherein $R^5$ a substituent selected from hydrogen, $C_{1-6}$ alkyl, $C_{1-6}$ alkoxy, $C_{1-6}$ alkenyl, $C_{1-6}$ alkynyl, $C_{1-6}$ alkanoyl, $C_{1-6}$ haloalkyl, $C_{1-6}$ haloalkenyl, $C_{1-6}$ haloalkynyl, $C_{1-6}$ haloalkoxy, $C_{1-6}$ haloalkylthiol, $C_{1-6}$ haloalkylsulfinyl, $C_{1-6}$ haloalkylsulfonyl, $C_{1-6}$ haloalkyl ketone, $C_{1-6}$ haloalkyl sulfinyl, $C_{1-6}$ haloalkyl sulfonyl, a polyethylene glycol (PEG) group, $C_{1-6}$ hydroxyalkyl, a nitrogen-containing $C_{2-10}$ alkyl and hydroxy;
$R^4$ is hydrogen, $C_{1-6}$ alkyl, $C_{1-6}$ alkanoyl, $C_{1-6}$ cycloalkyl, $C_{1-6}$ fluoroalkyl, hydroxy, or halogen;
$Y^1$ is S, SO, $SO_2$, or $CH_2$; and,
n is 0 to 10
"Alkyl", alone or in combination, means a straight-chain or branched-chain alkyl radical. Suitable alkyls include, but are not limited to methyl, ethyl, n-propyl, isopropyl, n-butyl, isobutyl, sec-butyl, tert-butyl, pentyl, iso-amyl, hexyl, octyl.

As used herein, the term "halogen" or "halo" includes iodine, fluorine, which are preferred, and chlorine and bromine.

"Heterocycle" means an aliphatic or aromatic saturated or partially unsaturated monocycle. Suitable heterocycles include, but are not limited to, furan, pyrrole, imidazole, triazole, thiophenol, pyridine, piperidine, pyran, and piperazine.

Where a substituent is a PEG group, the group suitably comprises between 5 and 20 ethylene glycol units and preferably between 5 and 10 ethylene glycol units.

For the compounds of Formula I defined above, there are potentially a number of chiral centres. The present invention therefore encompasses racemic and optically pure forms of any compounds of the invention with one chiral centre, as well as racemic, diastereomer and optically pure forms of any compounds of the invention with two chiral centres. Optically pure forms of these compounds are preferred.

Suitable salts according to the invention, include physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methanesulphonic, and para-toluenesulphonic acids.

Suitable solvates according to the invention include ethanol, water, saline, physiological buffer and glycol.

The term "labelled with an imaging moiety" means either (i) that one of the atoms of the compound of Formula I itself is an imaging moiety, or (ii) that a group comprising an imaging moiety is conjugated to the compound of Formula I. Where one of the atoms of the compound of Formula I itself is an imaging moiety, for example any of the carbons could be $^{11}C$, or any F could be $^{18}F$. Where a group comprising an imaging moiety is conjugated to the compound of Formula I, it may be incorporated directly via any suitable atom present in the compound. Examples of groups comprising an imaging moiety include metal complexes which comprise a metallic imaging moiety, or radioiodophenyl. Alternatively, where a group comprising an imaging moiety is conjugated to the compound of Formula I, it may be incorporated indirectly via a linker group of Formula -$(L^1)_m$- wherein:

each L is independently —CO—, —$CR_2$—, —CR=CR—, —C≡C—, —$CR_2CO_2$—, —$CO_2CR_2$—, —NR—, —NRCO—, —CONR—, —NR(C=O)NR—, —NR(C=S)NR—, —$SO_2NR$—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-12}$ arylene group, a $C_{3-12}$ heteroarylene group, an amino acid residue, a polyalkyleneglycol, polylactic acid or polyglycolic acid moiety;

m is an integer of value 1 to 5;

each R group is independently H or $C_{1-6}$ alkyl, $C_{3-10}$ alkylaryl, $C_{2-6}$ alkoxyalkyl, $C_{1-6}$ hydroxyalkyl, $C_{1-6}$ fluoroalkyl, or 2 or more R groups, together with the atoms to which they are attached form a carbocyclic, heterocyclic, saturated or unsaturated ring.

More detail relating to imaging moieties and groups comprising imaging moieties is provided below.

The following is a recitation of the preferred substituents for Formula I:

$X^1$ and $X^2$ are preferably both hydrogen.

$R^1$ and $R^2$ are preferably independently selected from $C_{1-6}$ alkyl, $C_{1-6}$ methoxyalkyl or $C_{1-6}$ alkoxy, are most preferably both $C_{1-6}$ alkyl, and are most especially preferably both ethyl.

$R^3$ is preferably hydrogen, $C_{1-6}$ alkyl, $C_{1-6}$ alkoxy, $C_{1-6}$ alkenyl, $C_{1-6}$ alkynyl, $C_{1-6}$ alkanoyl, $C_{1-6}$ fluoroalkyl, $C_{1-6}$ fluoroalkoxy, or is A-$C_{1-6}$ alkyl or A-$C_{1-6}$ fluoroalkyl wherein A is as defined previously, most preferably hydrogen, $C_{1-6}$ alkyl, $C_{1-6}$ alkoxy, $C_{1-6}$ alkenyl, $C_{1-6}$ alkynyl, acetyl, $C_{1-6}$ fluoroalkyl, or is A-$C_{1-6}$ alkyl or A-$C_{1-6}$ fluoroalkyl wherein for A, $R^6$ is a 5- or 6-membered N-containing heterocycle, and most especially preferably $C_{1-3}$ alkyl, $C_{1-6}$ alkoxy, $C_{1-3}$ alkenyl, $C_{1-3}$ alkynyl, acetyl or $C_{1-6}$ fluoroalkyl, or is A-$C_{1-6}$ fluoroalkyl wherein for A, $R^6$ is a 5-membered N-containing heterocycle.

$R^4$ is preferably hydrogen, $C_{1-6}$ alkyl, $C_{1-6}$ alkanoyl, $C_{1-6}$ cycloalkyl or $C_{1-6}$ fluoroalkyl, most preferably hydrogen, $C_{1-6}$ alkyl or $C_{1-6}$ alkanoyl and most especially preferably hydrogen or $C_{1-3}$ alkyl.

$Y^1$ is preferably S, $SO_2$ or $CH_2$, most preferably S or $SO_2$, and most especially preferably S.

n is preferably 0 to 5 and most preferably 0.

For preferred compounds of Formula I of the invention:
$X^1$ and $X^2$ are both hydrogen;
$R^1$ and $R^2$ are independently selected from $C_{1-6}$ alkyl, $C_{1-6}$ methoxyalkyl or $C_{1-6}$ alkoxy;
$R^3$ is hydrogen, $C_{1-6}$ alkyl, $C_{1-6}$ alkoxy, $C_{1-6}$ alkanoyl, $C_{1-6}$ alkenyl, $C_{1-6}$ alkynyl, or $C_{1-6}$ fluoroalkyl, or is A-$C_{1-6}$ alkyl, or A-$C_{1-6}$ fluoroalkyl wherein A is as defined previously;
$R^4$ is hydrogen, $C_{1-6}$ alkyl, $C_{1-6}$ acetyl, $C_{1-6}$ cycloalkyl or $C_{1-6}$ fluoroalkyl;
$Y^1$ is S, 502, or $CH_2$; and,
n is 0

For most preferred compounds of Formula I of the invention:
$X^1$ and $X^2$ are both independently hydrogen;
$R^1$ and $R^2$ are both $C_{1-6}$ alkyl;
$R^3$ is hydrogen, $C_{1-3}$ alkyl, $C_{1-3}$ alkoxy, $C_{1-3}$ alkanoyl, $C_{1-3}$ alkenyl, $C_{1-3}$ alkynyl, or $C_{1-6}$ fluoroalkyl, or is A-$C_{1-6}$ alkyl or A-$C_{1-6}$ fluoroalkyl wherein for A, $R^6$ is a 5- or 6-membered N-containing heterocycle;
$R^4$ is hydrogen, $C_{1-6}$ alkyl or $C_{1-6}$ acetyl;
$Y^1$ is 5 or 502; and,
n is 0

For most especially preferred compounds of Formula I of the invention:
$X^1$ and $X^2$ are both hydrogen;
$R^1$ and $R^2$ are both ethyl;
$R^3$ is hydrogen, methyl, ethyl, 2-methoxy-ethyl, prop-2-ynyl, isopropyl, isobutyl, 2-methyl-allyl, acetyl, or 4-fluorobutyl, or is or is A-$C_{1-6}$ fluoroalkyl wherein for A, $R^6$ is a 5-membered N-containing heterocycle;
$R^4$ is hydrogen;
$Y^1$ is S; and,
n is 0

An alternative embodiment of this aspect of the invention is a compound of Formula I or a salt or solvate thereof, wherein said compound is labelled with an imaging moiety, and wherein:
$X^1$ and $X^2$ are independently selected from hydrogen, halogen, $C_{1-6}$ alkoxy, $C_{1-6}$ alkyl;
$R^1$ and $R^2$ are independently selected from $C_{1-6}$ alkyl, $C_{1-6}$ aminoalkyl, $C_{1-6}$ methoxyalkyl, $C_{1-6}$ alkoxy, $C_{1-6}$ alkyl alcohols, a polyethylene glycol (PEG) group, $C_{3-10}$ cycloalkanes, $C_{3-10}$ cycloethers, and $C_{3-10}$ cycloamines;
$R^3$ is an optional substituent selected from hydrogen, $C_{1-6}$ alkyl, $C_{1-6}$ acetyl, $C_{1-6}$ fluoroalkyl, $C_{1-6}$ fluoroalkoxy, $C_{1-6}$ fluoroalkylsulfinyl, $C_{1-6}$ fluoroalkylsulfonyl, trifluoromethyl ketone, trifluoromethyl sulfinyl, trifluoromethyl sulfonyl, a polyethylene glycol (PEG) group, $C_{1-6}$ alkyl alcohols and hydroxy;

$R^4$ is hydrogen, $C_{1-6}$ alkyl, $C_{1-6}$ acetyl, $C_{1-6}$ cycloalkyl, $C_{1-6}$ fluoroalkyl, hydroxy, or halogen;

$Y^1$ is S, SO, $SO_2$, or $CH_2$; and, n is 0 to 10

The synthesis of compounds of Formula I that are not labelled with an imaging moiety may be carried out by methods described by Okubo et al [Bioorganic and Medicinal Chemistry 2004 12 3569-80].

Preferred sites for incorporation of an imaging moiety into a compound of Formula I and in the more specific aspects of the invention are any of $R^1$-$R^4$ and either of $X^1$ or $X^2$, as in compounds of Formulas II-Ivi:

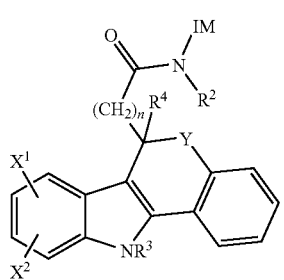
(Ii)

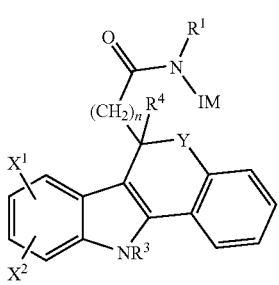
(Iii)

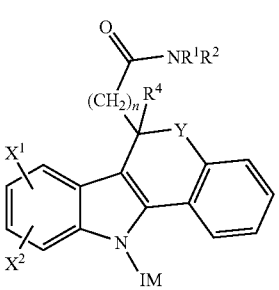
(Iiii)

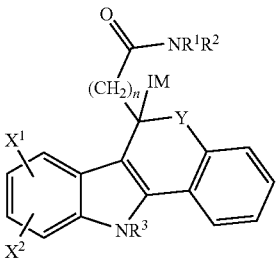
(Iiv)

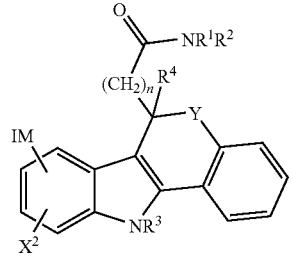
(Iv)

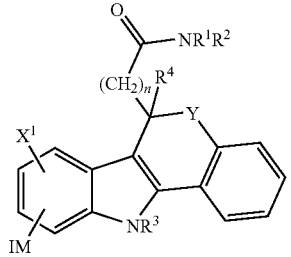
(Ivi)

wherein IM is an imaging moiety or a group comprising an imaging moiety and $R^1$-$R^4$, $X^1$, $X^2$ and $Y^1$ are as defined above for Formula I.

Most preferred sites for the incorporation of an imaging moiety into a compound of Formula I are $R^{1-3}$, and especially preferably $R^3$.

For $^{11}C$, a further preferred site of incorporation is at the carbonyl group bound to $NR^1R^2$, as in compounds of Formula Ivii:

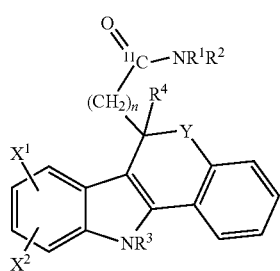
(Ivii)

wherein $R^1$-$R^4$, $X^1$, $X^2$ and $Y^1$ are as defined above for Formula I.

For radioiodine, a further preferred site of incorporation is at phenyl ring A' of Formula Iviii:

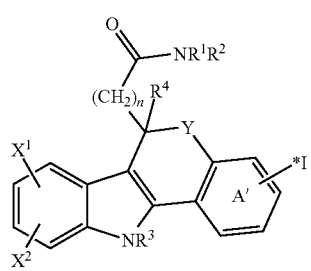
(Iviii)

Methods for incorporation of the preferred imaging moieties of the invention into a compound of Formula I are discussed below in relation to a further aspect of the invention.

The "imaging moiety" allows the compound of the invention to be detected using a suitable imaging modality following its administration to a mammalian body in vivo. Preferred imaging moieties of the invention are chosen from:

(i) a radioactive metal ion;
(ii) a paramagnetic metal ion;
(iii) a gamma-emitting radioactive halogen;
(iv) a positron-emitting radioactive non-metal;
(v) a hyperpolarised NMR-active nucleus;
(vi) a reporter suitable for in viva optical imaging;
(vii) a β-emitter suitable for intravascular detection.

When the imaging moiety is a radioactive metal ion, i.e. a radiometal, suitable radiometals can be either positron emitters such as $^{64}Cu$, $^{48}V$, $^{52}Fe$, $^{55}Co$, $^{94m}Tc$ or $^{68}Ga$; γ-emitters such as $^{99m}Tc$, $^{111}In$, $^{113m}In$, or $^{67}Ga$. Preferred radiometals are $^{99m}Tc$, $^{64}Cu$, $^{68}Ga$ and $^{111}In$. Most preferred radiometals are γ-emitters, especially $^{99m}Tc$.

When the imaging moiety is a paramagnetic metal ion, suitable such metal ions include: Gd(III), Mn(II), Cu(II), Cr(III), Fe(III), Co(III), Er(II), Ni(III), Eu(III) or Dy(III). Preferred paramagnetic metal ions are Gd(III), Mn(II) and Fe(III), with Gd(III) being especially preferred.

When the imaging moiety is a gamma-emitting radioactive halogen, the radiohalogen is suitably chosen from $^{123}I$, $^{131}I$ or $^{77}Br$. A preferred gamma-emitting radioactive halogen is $^{123}I$.

When the imaging moiety is a positron-emitting radioactive non-metal, suitable such positron emitters include: $^{11}C$, $^{13}N$, $^{15}O$, $^{17}F$, $^{18}F$, $^{75}Br$, $^{76}Br$ or $^{124}I$. Preferred positron-emitting radioactive non-metals are $^{11}C$, $^{13}N$, $^{18}F$ and $^{124}I$, especially $^{11}C$ and $^{18}F$, most especially $^{18}F$.

When the imaging moiety is a hyperpolarised NMR-active nucleus, such NMR-active nuclei have a non-zero nuclear spin, and include $^{13}C$, $^{15}N$, $^{19}F$, $^{29}Si$ and $^{31}P$. Of these, $^{13}C$ is preferred. By the term "hyperpolarised" is meant enhancement of the degree of polarisation of the NMR-active nucleus over its' equilibrium polarisation. The natural abundance of $^{13}C$ (relative to $^{12}C$) is about 1%, and suitable $^{13}C$-labelled compounds are suitably enriched to an abundance of at least 5%, preferably at least 50%, most preferably at least 90% before being hyperpolarised.

When the imaging moiety is a reporter suitable for in vivo optical imaging, the reporter is any moiety capable of detection either directly or indirectly in an optical imaging procedure. The reporter might be a light scatterer (e.g. a coloured or uncoloured particle), a light absorber or a light emitter. More preferably the reporter is a dye such as a chromophore or a fluorescent compound. The dye can be any dye that interacts with light in the electromagnetic spectrum with wavelengths from the ultraviolet light to the near infrared. Most preferably the reporter has fluorescent properties. Preferred organic chromophoric and fluorophoric reporters include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Particular examples of chromophores which may be used include: fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750.

When the imaging moiety is a β-emitter suitable for intravascular detection, suitable such β-emitters include the radiometals $^{67}Cu$, $^{89}Sr$, $^{90}Y$, $^{153}Sm$, $^{186}Re$, $^{188}Re$ or $^{192}Ir$, and the non-metals $^{32}P$, $^{33}P$, $^{38}S$, $^{38}Cl$, $^{39}Cl$, $^{82}Br$ and $^{83}Br$.

The most preferred imaging moieties of the invention are radioactive, especially radioactive metal ions, gamma-emitting radioactive halogens and positron-emitting radioactive non-metals, particularly those suitable for imaging using SPECT or PET. Most especially preferred imaging moieties of the invention are suitable for imaging using PET, i.e. $^{11}C$ and $^{18}F$.

Preferably, compounds of the invention have Ki values for binding to PBR (determined by method of Le Fur et al 1983 Life Sci. USA 33: 449-57) of between 0.01 nM and 10 nM, most preferably between 0.1 nM and 5.0 nM and most especially preferably between 0.1 nM and 1.0 nM.

Examples of most preferred compounds of Formula I labeled with an imaging moiety, are as follows:

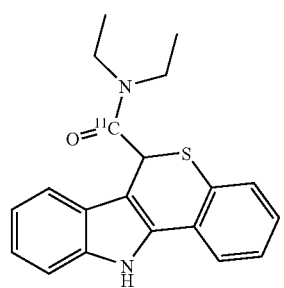

Compound 1

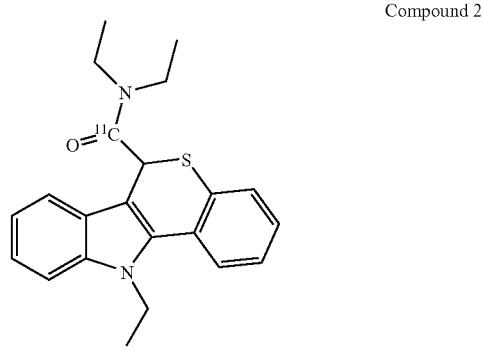

Compound 2

Compound 3
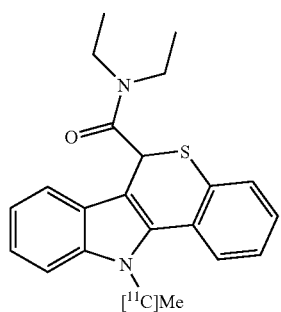
Compound 4
Compound 5
Compound 6
Compound 7
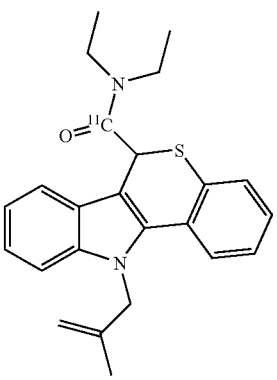
Compound 8
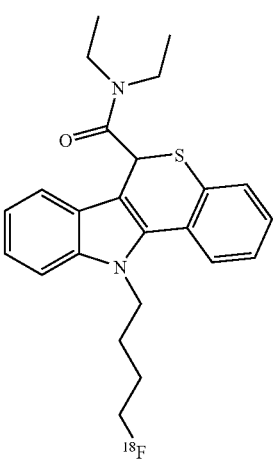
Compound 9
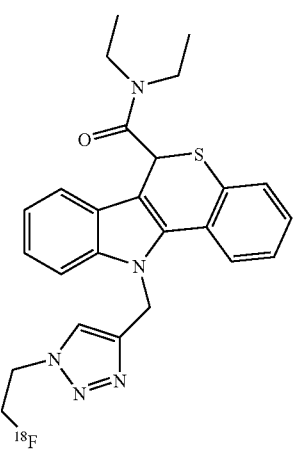
Compound 10
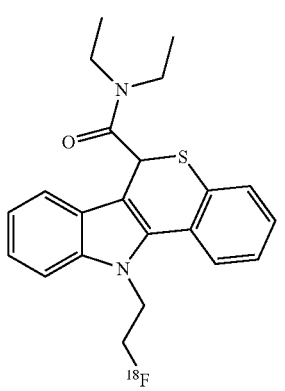

Compound 11

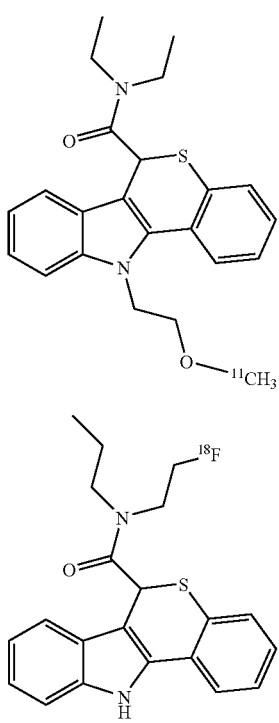

Compound 12

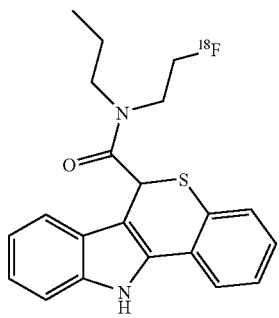

$K_i$ values for the best compounds, tested using the method of Example 18 below, were found to be between 1.0 nM and 0.1 nM.

Preferably, compounds of the invention do not undergo facile metabolism in vivo, and hence most preferably exhibit a half-life in viva of 60 to 240 minutes in humans. The compound is preferably excreted via the kidney (i.e. exhibits urinary excretion). The compound preferably exhibits a signal-to-background ratio at diseased foci of at least 1.5, most preferably at least 5, with at least 10 being especially preferred. Where the compound comprises a radioisotope, clearance of one half of the peak level of compound which is either non-specifically bound or free in vivo, preferably occurs over a time period less than or equal to the radioactive decay half-life of the radioisotope of the imaging moiety.

The molecular weight of the compound is preferably up to 5000 Daltons. Most preferably, the molecular weight is in the range 150 to 3000 Daltons, most especially preferably 200 to 1500 Daltons, with 300 to 800 Daltons being ideal.

In a further aspect, the present invention provides a compound of Formula II:

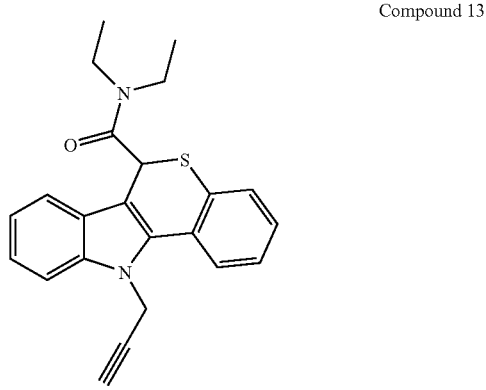 (II)

or a salt or solvate thereof wherein:

$R^7$ is as defined previously for $R^3$, with the proviso that $R^7$ is not hydrogen, $C_{1-5}$ alkyl or a nitrogen-containing $C_{2-10}$ alkyl group; and, $Y^2$ is as defined for $Y^1$ above.

The synthesis of compounds of Formula II may be carried out by adapting the methods described by Okubo et al [Bioorganic and Medicinal Chemistry 2004 12 3569-80].

Examples of preferred compounds of Formula II are as follows:

Compound 13

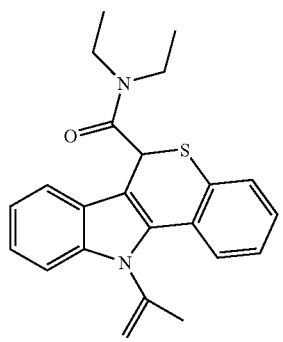

Compound 14

Compound 15

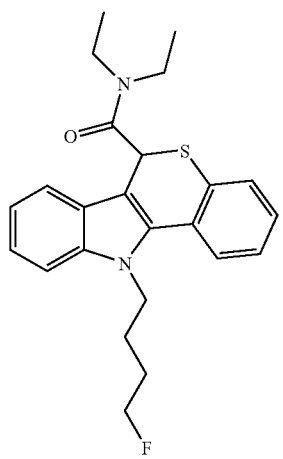

Compound 16

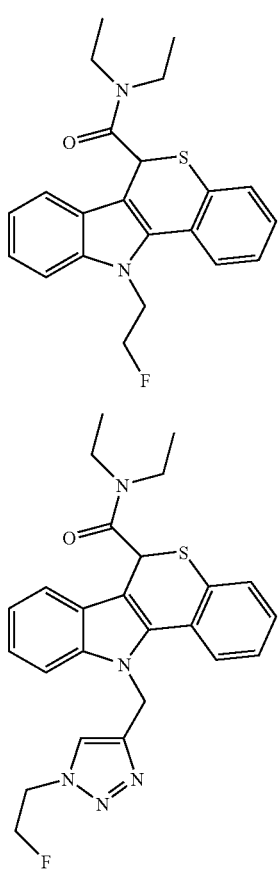

Compound 17

K_i values for the best compounds, tested using the method of Example 18 below, were found to be between 1.0 nM and 0.1 nM.

In another further aspect, the present invention provides a method for the preparation of a compound of Formula I labelled with an imaging moiety comprising reaction of a convenient chemical form of an imaging moiety with a precursor of Formula Ia:

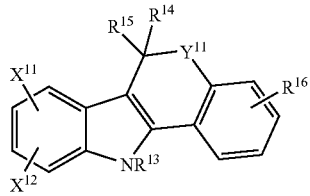

(Ia)

wherein:
$X^{11}$, $X^{12}$, $R^{13}$, $R^{14}$ and $Y^{11}$ are as defined for $X^1$, $X^2$, $R^3$, $R^4$ and $Y^{11}$, respectively, of Formula I above, or independently comprise a suitable protecting group;

$R^{15}$ is the group —$(CH_2)_o$—$C(=O)$—$NR^{11}R^{12}$ wherein o, $R^{11}$ and $R^{12}$ are as defined for n, $R^1$ and $R^2$ respectively for Formula I, or comprises a suitable protecting group; and, $R^{16}$ is hydrogen, and provided that at least one of $X^{11}$, $X^{12}$ and $R^{11}$-$R^{16}$ comprises a chemical group capable of reacting with a suitable source of said imaging moiety, said chemical group which:

(i) is capable of completing a metallic imaging moiety;
(ii) comprises an organometallic derivative such as a trialkylstannane or a trialkylsilane;
(iii) comprises a derivative containing an alkyl halide or an alkyl sulfonate (such as alkyl tosylate or alkyl mesylate) for nucleophilic substitution;
(iv) comprises a derivative containing an aromatic ring activated towards nucleophilic or electrophilic substitution;
(v) comprises a derivative containing a functional group which undergoes facile alkylation; or,
(vi) comprises a derivative which alkylates thiol-containing compounds to give a thioether-containing product.

A "precursor" comprises a derivative of the compound of Formula I, designed so that chemical reaction with a convenient chemical form of the imaging moiety occurs site-specifically; can be conducted in the minimum number of steps (ideally a single step); and without the need for significant purification (ideally no further purification), to give the desired imaging agent. Such precursors are synthetic and can conveniently be obtained in good chemical purity. The "precursor" may optionally comprise a protecting group for certain functional groups of the compound of Formula Ia.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tetrabutyldimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999).

When the imaging moiety comprises a metal ion, the precursor is derivatised to include a chemical group capable of complexing the metal ion to form a metal complex. By the term "metal complex" is meant a coordination complex of the metal ion with one or more ligands. It is strongly preferred that the metal complex is "resistant to transchelation", i.e. does not readily undergo ligand exchange with other potentially competing ligands for the metal coordination sites. Potentially competing ligands include the compound of Formula I itself plus other excipients in the preparation in vitro (e.g. radioprotectants or antimicrobial preservatives used in the preparation), or endogenous compounds in vivo (e.g. glutathione, transferrin or plasma proteins).

Suitable ligands for use in the present invention which form metal complexes resistant to transchelation include: chelating agents, where 2-6, preferably 2-4, metal donor atoms are arranged such that 5- or 6-membered chelate rings result (by having a non-coordinating backbone of either carbon atoms or non-coordinating heteroatoms linking the metal donor atoms); or monodentate ligands which comprise donor atoms which bind strongly to the metal ion, such as isonitriles, phosphines or diazenides. Examples of donor atom types which bind well to metals as part of chelating agents are: amines, thiols, amides, oximes and phosphines. Phosphines form such strong metal complexes that even monodentate or bidentate phosphines form suitable metal complexes. The linear geometry of isonitriles and diazenides is such that they do not lend themselves readily to incorporation into chelating agents, and are hence typically used as monodentate ligands. Examples of suitable isonitriles include simple alkyl isonitriles such as tert-butylisonitrile, and ether-substituted isonitriles such as mibi (i.e. 1-isocyano-2-methoxy-2-methylpropane). Examples of suitable phosphines include Tetrofosmin, and monodentate phosphines such as tris(3-methoxypropyl) phosphine. Examples of suitable diazenides include the HYNIC series of ligands i.e. hydrazine-substituted pyridines or nicotinamides.

Examples of suitable chelating agents for technetium which form metal complexes resistant to transchelation include, but are not limited to:

(i) diaminedioximes of Formula III:

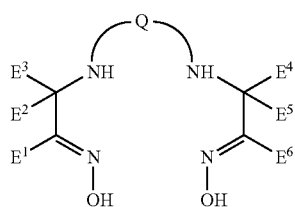

(III)

where $E^1$-$E^6$ are each independently an R* group;

each R* is H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, $C_{2-10}$ carboxyalkyl or $C_{1-10}$ aminoalkyl, or two or more R* groups together with the atoms to which they are attached form a carbocyclic, heterocyclic, saturated or unsaturated ring, and wherein one or more of the R* groups is conjugated to the vector;

and Q is a bridging group of formula -(J)$_f$-;

where f is 3, 4 or 5 and each J is independently —O—, —NR*— or —C(R*)$_2$—, wherein R* is as previously defined, provided that -(J)$_f$- contains a maximum of one J group which is —O— or —NR*—.

Preferred Q groups are as follows:

Q=—(CH$_2$)(CHR*)(CH$_2$)— i.e. propyleneamine oxime or PnAO derivatives;

Q=—(CH$_2$)$_2$(CHR*)(CH$_2$)$_2$— i.e. pentyleneamine oxime or PentAO derivatives;

Q=—(CH$_2$)$_2$NR*(CH$_2$)$_2$—.

$E^1$ to $E^6$ are preferably chosen from: $C_{1-3}$ alkyl, alkylaryl alkoxyalkyl, hydroxyalkyl, fluoroalkyl, carboxyalkyl or aminoalkyl. Most preferably, each $E^1$ to $E^6$ group is $CH_3$.

The compound of the invention is preferably conjugated at either the $E^1$ or $E^6$ R* group, or an R* group of the Q moiety. Most preferably, it is conjugated to an R* group of the Q moiety. When it is conjugated to an R* group of the Q moiety, the R* group is preferably at the bridgehead position. In that case, Q is preferably —(CH$_2$)(CHR*)(CH$_2$)—, —(CH$_2$)$_2$(CHR*)(CH$_2$)$_2$— or —(CH$_2$)$_2$NR*(CH$_2$)$_2$—, most prefer ably —(CH$_2$)$_2$(CHR*)(CH$_2$)$_2$—. An especially preferred bifunctional diaminedioxime chelator has the Formula IV:

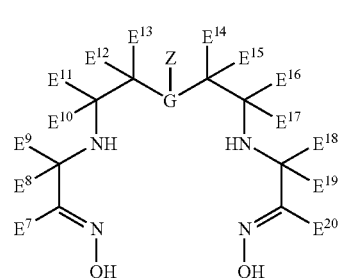

(IV)

where:
$E^7$-$E^{20}$ are each independently an R* group as previously defined;
G is N or $CE^{21}$ wherein $E^{21}$ is an R* group as previously defined;
Z is the site of linkage to a compound of Formula I and may comprise a linker group -(L$^2$)$_r$- wherein each L$^2$ is independently —O—, —NR*—, —C(R*)$_2$—, or a $C_{5-12}$ arylene group wherein R* is as previously defined, and r is an integer between 1 and 5.

A preferred chelator of Formula IV is of Formula IVa:

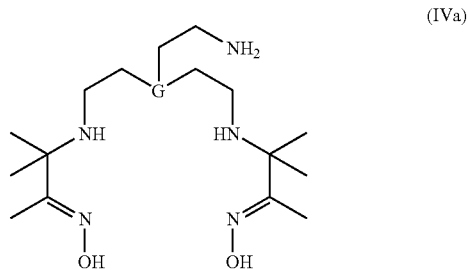

(IVa)

where G is as defined above;
such that the compound of Formula I is conjugated via the bridgehead —CH$_2$CH$_2$NH$_2$ group.

Further suitable chelators of the invention include:
(ii) N$_3$S ligands having a thioltriamide donor set such as MAG$_3$ (mercaptoacetyltriglycine) and related ligands; or having a diamidepyridinethiol donor set such as Pica;
(iii) N$_2$S$_2$ ligands having a diaminedithiol donor set such as BAT or ECD (i.e. ethylcysteinate dimer), or an amideaminedithiol donor set such as MAMA;
(iv) N$_4$ ligands which are open chain or macrocyclic ligands having a tetramine, amidetriamine or diamidediamine donor set, such as cyclam, monoxocyclam or dioxocyclam.
(v) N$_2$O$_2$ ligands having a diaminediphenol donor set.

The above described ligands are particularly suitable for complexing technetium e.g. $^{94m}$Tc or $^{99m}$Tc, and are described more fully by Jurisson et al [Chem. Rev., 99, 2205-2218 (1999)]. The ligands are also useful for other metals, such as copper ($^{64}$Cu or $^{67}$CU), vanadium (e.g. $^{48}$V), iron leg. $^{52}$Fe), or cobalt (e.g. $^{55}$Co). Other suitable ligands are described in Sandoz WO 91/01144, which includes ligands which are particularly suitable for indium, yttrium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. When the radiometal ion is technetium, the ligand is preferably a chelating agent which is tetradentate. Preferred chelating agents for technetium are the diaminedioximes, or those having an N₂S₂ or N₃S donor set as described above.

It is envisaged that the role of the linker group -(L₂)ᵣ- is to distance the relatively bulky technetium complex, which results upon metal coordination, from the active site of the compound of Formula I so that e.g. receptor binding is not impaired.

Preferred linker groups -(L²)ᵣ- in the context of these chelators have a backbone chain (i.e. the linked atoms which make up the -(L₂)ᵣ- moiety) which contains 2 to 5 atoms, with 2 or 3 atoms being most preferred. A minimum linker group backbone chain of 2 atoms confers the advantage that the aza-diaminedioxime chelator is well-separated from the biological targeting moiety so that any interaction is minimised. Furthermore, the vector is unlikely to compete effectively with the coordination of the chelator to the metal ion. In this way, both the biological targeting characteristics of the vector, and the metal complexing capability of the chelator is maintained. It is strongly preferred that the compound of Formula I is bound to the chelator in such a way that the linkage does not undergo facile metabolism in blood. That is because such metabolism would result in the imaging metal complex being cleaved off before the labelled compound reaches the desired in vivo target site. The compound of Formula I is therefore preferably covalently bound to the metal complexes of the present invention via -(L²)ᵣ- linker groups which are not readily metabolised.

Non-peptide linker groups such as alkylene groups or arylene groups have the advantage that there are no significant hydrogen bonding interactions with the conjugated compound of Formula I so that the linker does not wrap round onto the compound. Preferred alkylene spacer groups are —(CH₂)_q— where q is an integer of value 2 to 5. Preferably q is 2 or 3. Preferred arylene spacers are of formula:

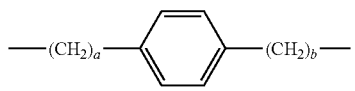

where: a and b are each independently 0, 1 or 2.

When the imaging metal is technetium, the usual technetium starting material is pertechnetate, i.e. TcO₄⁻ which is technetium in the Tc(VII) oxidation state. Pertechnetate itself does not readily form metal complexes, hence the preparation of technetium complexes usually requires the addition of a suitable reducing agent such as stannous ion to facilitate complexation by reducing the oxidation state of the technetium to the lower oxidation states, usually Tc(I) to Tc(V). The solvent may be organic or aqueous, or mixtures thereof. When the solvent comprises an organic solvent, the organic solvent is preferably a biocompatible solvent, such as ethanol or DMSO. Preferably the solvent is aqueous, and is most preferably isotonic saline.

Where the imaging moiety is radioiodine, preferred precursors are those which comprise a derivative which either undergoes electrophilic or nucleophilic iodination or undergoes condensation with a labelled aldehyde or ketone. Examples of the first category are:
    (a) organometallic derivatives such as a trialkylstannane (e.g. trimethylstannyl or tributylstannyl), or a trialkylsilane (e.g. trimethylsilyl) or an organoboron compound (e.g. boronate esters or organotrifluoroborates);
    (b) a non-radioactive alkyl bromide for halogen exchange or alkyl tosylate, mesylate or triflate for nucleophilic iodination;
    (c) aromatic rings activated towards electrophilic iodination (e.g. phenols) and aromatic rings activated towards nucleophilic iodination (e.g. aryl iodonium salt aryl diazonium, aryl trialkylammonium salts or nitroaryl derivatives).

For radioiodination, the precursor preferably comprises: an aryl iodide or bromide (to permit radioiodine exchange); an activated precursor aryl ring (e.g. a phenol group); an organometallic precursor compound (e.g. trialkyltin, trialkylsilyl or organoboron compound); or an organic precursor such as triazenes or a good leaving group for nucleophilic substitution such as an iodonium salt. Precursors and methods of introducing radioiodine into organic molecules are described by Bolton [J. Lab. Comp. Radiopharm., 45, 485-528 (2002)]. Precursors and methods of introducing radioiodine into proteins are described by Wilbur [Bioconj. Chem., 3(6), 433-470 (1992)]. Suitable boronate ester organoboron compounds and their preparation are described by Kabalaka et al [Nucl. Med. Biol., 29, 841-843 (2002) and 30, 369-373 (2003)]. Suitable organotrifluoroborates and their preparation are described by Kabalaka et al [Nucl. Med. Biol., 31, 935-938 (2004)]. Preferred precursors for radioiodination comprise an organometallic precursor compound, most preferably a trialkyltin.

Examples of aryl groups to which radioactive iodine can be attached are given below:

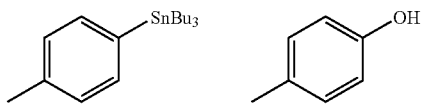

Both contain substituents which permit facile radioiodine substitution onto the aromatic ring. Alternative substituents containing radioactive iodine can be synthesised by direct iodination via radiohalogen exchange, e.g.

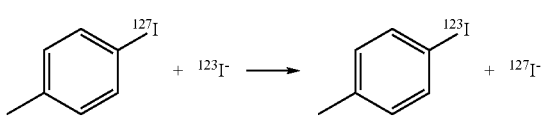

Examples of precursor compounds of Formula I derivatised to include the above aryl groups are as follows:

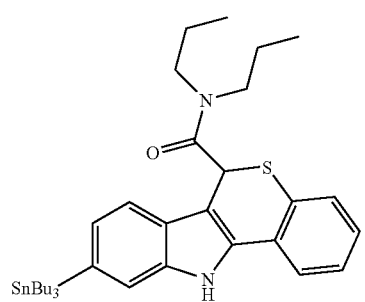

-continued

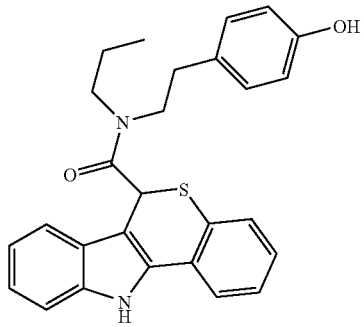

-continued

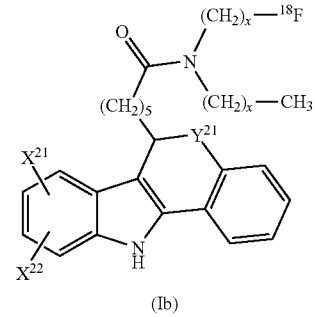

(Ib)

The radioiodine atom is preferably attached via a direct covalent bond to an aromatic ring such as a benzene ring, or a vinyl group since it is known that iodine atoms bound to saturated aliphatic systems are prone to in vivo metabolism and hence loss of the radioiodine.

When the imaging moiety is a radioactive isotope of fluorine the radiofluorine atom may form part of a fluoroalkyl or fluoroalkoxy group, since alkyl fluorides are resistant to in vivo metabolism. Alternatively, the radiofluorine atom may attach via a direct covalent bond to an aromatic ring such as a benzene ring. Radiofluorination may be carried out via direct labelling using the reaction of $^{18}$F-fluoride with a suitable chemical group in the precursor having a good leaving group, such as an alkyl bromide, alkyl mesylate or alkyl tosylate. $^{18}$F can also be introduced by O-alkylation of hydroxyl groups with $^{18}$F(CH$_2$)$_3$OMs or $^{18}$F(CH$_2$)$_3$Br. $^{18}$F can also be introduced by alkylation of N-haloacetyl groups with a $^{18}$F(CH$_2$)$_3$OH reactant, to give —NH(CO)CH$_2$—O—(CH$_2$)$_3$$^{18}$F derivatives. For aryl systems, $^{18}$F-fluoride nucleophilic displacement from an aryl diazonium salt, aryl nitro compound or an aryl quaternary ammonium salt are suitable routes to aryl-$^{18}$F derivatives.

A $^{18}$F-labelled compound of the invention of Formula Ib may be obtained by formation of $^{18}$F fluorodialkylamines and subsequent amide formation as shown in the following reaction scheme:

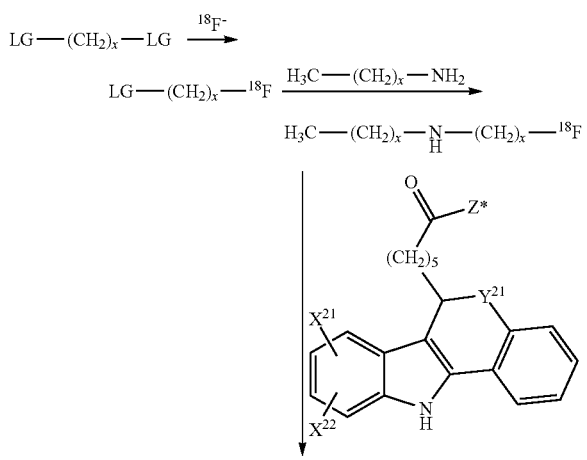

wherein $X^{21}$, $X^{22}$, $Y^{21}$ and s are the same as $X^1$, $X^2$, $Y^1$ and n, respectively, described previously for Formula I; and LG is a suitable leaving group, e.g. Cl, Br, I, OTs, OMs, or OTf;

Z* is e.g. Cl, P(O)Ph$_3$, or an activated ester; and, x=0-6.

Alternatively, labeling with $^{18}$F can be achieved by nucleophilic displacement of a leaving group (LG as defined above) from a derivative of Formula I. Such derivatives are precursors for the preparation of in vivo imaging compounds of the invention. Another strategy would be to have a leaving group (LG, as defined above) in place on an alkylamide group present on the precursor. In this way, the precursor compound may be labeled in one step by reaction with a suitable source of [$^{18}$F]-fluoride ion ($^{18}$F$^-$), which is normally obtained as an aqueous solution from the nuclear reaction $^{18}$O(p,n)$^{18}$F and is made reactive by the addition of a cationic counterion and the subsequent removal of water. For this method, the precursor compounds are normally selectively chemically protected so that radiofluorination takes place at a particular site on the compound. Suitable protecting groups are those already mentioned previously.

$^{11}$C-labelled PET tracer compounds may be synthesised by reacting a precursor with $^{11}$C methyl iodide. As the half-life of $^{11}$C is only 20.4 minutes, it is important that the intermediate $^{11}$C methyl iodide has high specific activity and, consequently, that it is produced using a reaction process which is as rapid as possible. A thorough review of such $^{11}$C-labelling techniques may be found in Antoni et al "Aspects on the Synthesis of $^{11}$C-Labelled Compounds" in Handbook of Radiopharmaceuticals, Ed. M. J. Welch and C. S. Redvanly (2003, John Wiley and Sons).

A $^{11}$C-labelled compound of Formula Ic may be obtained by employing the following reaction scheme:

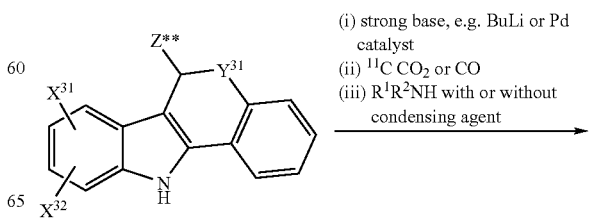

(i) strong base, e.g. BuLi or Pd catalyst
(ii) $^{11}$C CO$_2$ or CO
(iii) R$^1$R$^2$NH with or without condensing agent

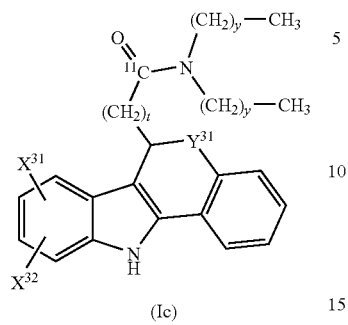

(Ic)

wherein $X^{31}$, $X^{32}$, $Y^{31}$ and t are as described previously for $X^1$, $X^2$, $Y^1$ and n, respectively of Formula I; and
Z** is a substrate suitable for transition metal catalysts, e.g. hydrogen, halide, boronic acid, OTf, organotin; and,
y=0-6.

The precursor is ideally provided in sterile, apyrogenic form. The precursor can accordingly be used for the preparation of a pharmaceutical composition and is also suitable for inclusion as a component in a kit for the preparation of a pharmaceutical composition. These aspects are discussed in more detail below in relation to additional aspects of the invention.

In a further preferred embodiment of the method of the invention, the precursor is bound to a solid phase. The precursor is preferably supplied covalently attached to a solid support matrix. In this way, the desired product forms in solution, whereas starting materials and impurities remain bound to the solid phase. As an example of such a system, precursors for solid phase electrophilic fluorination with $^{18}$F-fluoride are described in WO 03/002489, and precursors for solid phase nucleophilic fluorination with $^{18}$F-fluoride are described in WO 03/002157.

The Examples section below describes some methods for preparation of compounds of the invention where certain precursors are used:
Example 5 uses 6,11-dihydro-5-thia-11-aza-benzo[α]fluorene-6-carboxylic acid propylamide as a precursor in the synthesis of Compound 12.
Example 14 uses 11-(2-Tosyloxy-ethyl)-6,11-dihydro-5-thia-11-aza-benzo[α]fluorene-6-carboxylic acid diethylamide as a precursor in the synthesis of Compound 10.
Example 17 uses 11-(2-hydroxy-ethyl)-6,11-dihydro-5-thia-11-aza-benzo[α]fluorine-6-carboxylic acid diethylamide as a precursor in the synthesis of Compound 11.

In a further aspect, the invention provides a precursor for the preparation of the in vivo imaging compound of the invention wherein said precursor is of Formula Ia as defined above, and wherein said chemical group capable of reacting with said imaging moiety:
  (i) is capable of complexing a metallic imaging moiety;
  (ii) comprises an organometallic derivative such as a trialkylstannane or a trialkylsilane;
  (iii) comprises a derivative containing an alkyl halide or an alkyl sulfonate (such as alkyl tosylate or alkyl mesylate) for nucleophilic substitution;
  (iv) comprises a derivative which alkylates thiol-containing compounds to give a thioether-containing product.

Preferably, said chemical group is capable of reacting with an imaging moiety suitable for PET imaging. Examples of such preferable precursors are as follows:

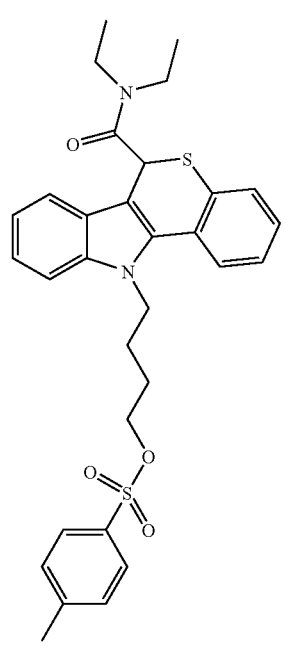

Compound 8P

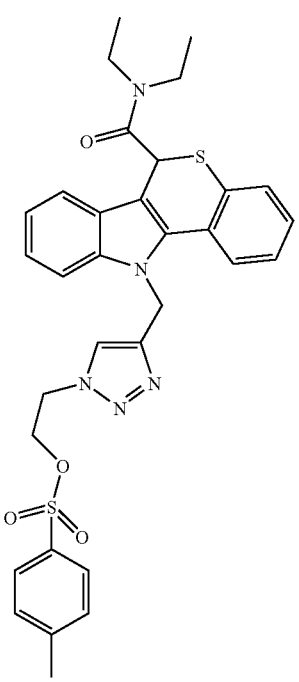

Compound 9P$^1$

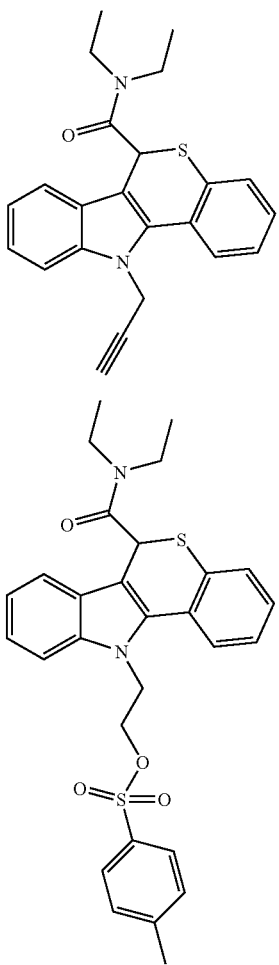

Compound 9P²

Compound 10P where Compound 8P is a precursor for the preparation of Compound 8, Compounds 9P¹ and 9P² (also non-radioactive Compound 6) are precursors for the preparation of Compound 9, and Compound 10P is a precursor for the preparation of Compound 10.

In another further aspect, the present invention provides a pharmaceutical composition which comprises a compound of the invention together with a biocompatible carrier in a form suitable for mammalian administration.

Where the pharmaceutical composition comprises a compound of Formula I labelled with an imaging moiety, the "biocompatible carrier" is a fluid, especially a liquid, in which the compound is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

Such pharmaceutical compositions comprising a compound of Formula I labelled with an imaging moiety are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm³ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use.

Preferably, where the compound is a compound of Formula I labelled with an imaging moiety, the pharmaceutical composition is a radiopharmaceutical composition. For radiopharmaceutical compositions, the pre-filled syringe may optionally be provided with a syringe shield to protect the operator from radioactive dose. Suitable such radiopharmaceutical syringe shields are known in the art and preferably comprise either lead or tungsten.

The radiopharmaceuticals may be administered to patients for SPECT or PET imaging in amounts sufficient to yield the desired signal, typical radionuclide dosages of 0.01 to 100 mCi, preferably 0.1 to 50 mCi will normally be sufficient per 70 kg bodyweight.

The pharmaceutical composition comprising a compound of Formula I labelled with an imaging moiety may be prepared from kits, as is described below. Alternatively, such a pharmaceutical composition may be prepared under aseptic manufacture conditions to give the desired sterile product. This pharmaceutical composition may also be prepared under non-sterile conditions, followed by terminal sterilisation using e.g. gamma-irradiation, autoclaving, dry heat or chemical treatment (e.g. with ethylene oxide). Preferably, the pharmaceutical composition comprising the compound of Formula I labelled with an imaging moiety is prepared from a kit.

Where the pharmaceutical composition comprises the compound of Formula II the biocompatible carrier may be a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerols solutions are also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained release formulations and the like. Suitable pharmaceutical carriers are described in "Remington's Pharmaceutical Sciences" by E. W. Martin. Such compositions will contain an effective therapeutic amount of the compound together with a suitable amount of carrier so as to provide the form for proper administration to the host. While intravenous injection is a very effective form of administration, other modes can be employed, e.g. oral administration.

The posology depends on the effects required and the method of administration used. For example, by the oral route, it may be between 20 and 100 mg of active substance per day, with unit doses of from 5 to 200 mg.

In a yet further aspect, the present invention provides kits for the preparation of the pharmaceutical compositions wherein the compound is a compound of Formula I labelled with an imaging moiety. Such kits comprise a suitable precursor as described above, preferably in sterile non-pyrogenic form, so that reaction with a sterile source of an imaging moiety gives the desired pharmaceutical with the minimum number of manipulations. Such considerations are particularly important for radiopharmaceuticals, in particular where the radioisotope has a relatively short half-life, and for ease of handling and hence reduced radiation dose for the radiopharmacist. Hence, the reaction medium for reconstitution of such kits is preferably a "biocompatible carrier" as defined above, and is most preferably aqueous.

Suitable kit containers comprise a sealed container which permits maintenance of sterile integrity and/or radioactive safety, plus optionally an inert headspace gas (e.g. nitrogen or argon), whilst permitting addition and withdrawal of solutions by syringe. A preferred such container is a septum-sealed vial, wherein the gas-tight closure is crimped on with an overseal (typically of aluminium). Such containers have the additional advantage that the closure can withstand vacuum if desired e.g. to change the headspace gas or degas solutions.

In the case of precursors bound to a solid phase, the sealed container may be a cartridge provided as part of the kit, which can be plugged into a suitably adapted automated synthesizer. The cartridge may contain, apart from the solid support-bound precursor, a column to remove unwanted fluoride ion, and an appropriate vessel connected so as to allow the reaction mixture to be evaporated and allow the product to be formulated as required. These cartridges are especially useful for the preparation of compounds of the invention labeled with short-lived radioisotopes such as $^{11}$C or $^{18}$F.

Preferred embodiments of the precursor when employed in the kit are as described above. The precursors for use in the kit may be employed under aseptic manufacture conditions to give the desired sterile, non-pyrogenic material. The precursors may also be employed under non-sterile conditions, followed by terminal sterilisation using e.g. gamma-irradiation, autoclaving, dry heat or chemical treatment (e.g. with ethylene oxide). Preferably, the precursors are employed in sterile, non-pyrogenic form. Most preferably the sterile, non-pyrogenic precursors are employed in the sealed container as described above.

For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. Suitable kits comprise a container (e.g. a septum-sealed vial) containing the uncomplexed chelating agent, together with a pharmaceutically acceptable reducing agent such as sodium dithionite, sodium bisulphite, ascorbic acid, formamidine sulphinic acid, stannous ion, Fe(II) or Cu(I); together with at least one salt of a weak organic acid with a biocompatible cation. By the term "biocompatible cation" is meant a positively charged counterion which forms a salt with an ionised, negatively charged group, where said positively charged counterion is also non-toxic and hence suitable for administration to the mammalian body, especially the human body.

Examples of suitable biocompatible cations include: the alkali metals sodium or potassium; the alkaline earth metals calcium and magnesium; and the ammonium ion. Preferred biocompatible cations are sodium and potassium, most preferably sodium.

The kits may optionally further comprise additional components such as a radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation. The "biocompatible cation" and preferred embodiments thereof are as described above.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the pharmaceutical composition post-reconstitution, i.e. in the radioactive imaging product itself. The antimicrobial preservative may, however, also optionally be used to inhibit the growth of potentially harmful micro-organisms in one or more components of the non-radioactive kit of the present invention prior to reconstitution. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parobens.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [i.e. tris (hydroxymethyl)aminomethane], and pharmaceutically acceptable bases such as sodium carbonate, sodium bicarbonate or mixtures thereof. When the conjugate is employed in acid salt form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The compounds of the invention are useful for in vivo imaging. Accordingly, in an even further aspect, the present invention provides a compound of the invention for use in an in vivo imaging method, such as SPECT or PET, which are preferred, and magnetic resonanace imaging (MRI) or optical imaging. The imaging method may be used to study PBR in healthy subjects, or in subjects known or suspected to have a pathological condition associated with abnormal expression of PBR (a "PBR condition"). Preferably, said method relates to the in vivo imaging of a subject suspected to have a PBR condition, and therefore has utility in the diagnosis of said condition. Examples of such PBR conditions where in viva imaging would be of use include neuropathologies such as Parkinson's disease, multiple sclerosis, Alzheimer's disease and Huntington's disease where neuroinflammation is present. Other PBR conditions that may be usefully imaged with the compounds of the invention include neuropathic pain, arthritis, asthma, atherosclerosis and cancer.

This aspect of the invention also provides a method for the in vivo diagnosis or imaging of a PBR condition in a subject, comprising administration of a pharmaceutical composition comprising a compound of the invention. Said subject is preferably a mammal and most preferably a human. In an alternative embodiment, this aspect of the invention furthermore provides for the use of the compound of the invention for imaging in vivo in a subject of a PBR condition wherein said subject is previously administered with the pharmaceutical composition comprising a compound of Formula I labelled with an imaging moiety.

By "previously administered" is meant that the step involving the clinician, wherein the imaging agent is given to the patient e.g., intravenous injection, has already been carried out. This aspect of the invention includes the use of a compound of Formula I labelled with an imaging moiety for the manufacture of diagnostic agent for the diagnostic imaging in vivo of a PBR condition.

Furthermore, this aspect of the invention provides for use of the compound of the invention in the manufacture of a pharmaceutical for the in vivo diagnosis or imaging of a PBR condition.

The compounds of Formula I may also be used for in vivo imaging of PBR in human and animal subjects in the context of their use as research tools. For example, for the performance of competition studies which allow the interaction of a drug with PBR to be studied. Such studies include dose-occupancy studies, determination of optimal therapeutic dose, drug candidate selection studies, and determination of PBR distribution in the tissue of interest.

In another aspect the invention provides a method of monitoring the effect of treatment of a human or animal body with a drug to combat a PBR condition, said method comprising administering to said body a compound of Formula I labelled with an imaging moiety and detecting the uptake of said compound, said administration and detection optionally but preferably being effected repeatedly, e.g. before, during and after treatment with said drug.

In a further aspect, the present invention provides a method for the treatment of a PBR condition in a mammal, preferably a human, by administration of a pharmaceutical composition comprising the compound of Formula II. Details of the nature of such a pharmaceutical composition, its administration and dosage are described above.

BRIEF DESCRIPTION OF THE EXAMPLES

Example 1 describes an alternative synthetic route to Okubo et al for obtaining 6,11-Dihydro-5-thia-11-aza-benzo[α]fluorene-6-carboxylic acid diethylamide (this is a non-radioactive version of Compound 1 of the invention). The alternative synthesis could be easily adapted to obtain other compounds of Formula I. An increased yield of product (54%) was obtained using this method compared with the method of Okubo et al.

Example 2 describes the synthesis of a chelate of Formula IIIa wherein G is C. This chelate is suitable for forming a complex with $^{99m}$Tc.

Example 3 describes how to conjugate the chelate of Example 1 to a compound of Formula I to obtain a precursor compound of the invention.

Example 4 describes how the precursor compounds obtained by the method of Example 2 can be labelled with $^{99m}$Tc in order to obtain compounds of the invention.

Example 5 describes the synthesis of a precursor compound suitable for reaction with $^{18}$F and how to label the precursor compound with $^{18}$F to form a Compound 12.

Example 6 describes the synthesis of a precursor compound suitable for reaction with $^{11}$C and how to label the precursor compound with $^{11}$C to form a compound of the invention.

Examples 7-13 describe how to obtain non-radioactive versions of Compounds 3-9 of the invention.

Example 14 describes how to obtain a non-radioactive version of Compound 10 via a route which may by analogy be used to obtain the radioactive version.

Example 15 describes the synthetic route used to obtain Compound 10.

Example 16 describes how to obtain a non-radioactive version of Compound 11 via a route which by analogy may be used to obtain the radioactive version.

Example 17 is a prophetic example describing a method suitable for the preparation of Compound 11.

Example 18 describes the method used to screen the compounds of the invention for their affinity to PBR.

EXAMPLES

Example 1

Synthesis of 6,11-Dihydro-5-thia-11-aza-benzo[α]fluorene-6-carboxylic acid diethylamide (non-radioactive Compound 1)

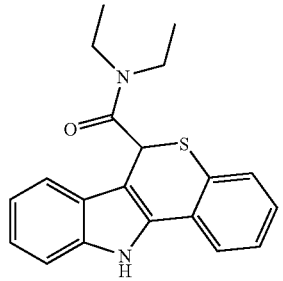 [SMILES: CCN(CC)C(=O)C1Sc2ccccc2-c2[nH]c3ccccc3c21]

a) 3-Phenylsulfanyl-dihydro-furan-2,5-dione

Triethylamine (0.8 ml) was added dropwise to a solution of benzenethiol (9.3 ml, 91 mmol) and maleic anhydride (8.9 g, 91 mmol) in toluene (125 ml). After stirring at room temperature for 12 hr the solvent was evaporated to leave 20 g of crude 3-phenylsulfanyl-dihydro-furan-2,5-dione as a brown oil. $^1$H NMR (CDCl$_3$) δ 7.20-7.70 (5H, m), 4.20 (1H, dd), 3.40 (1H, dd), 2.90 (1H, dd).

b) 4-Oxo-thiochroman-2-carboxylic acid

Crude 3-phenylsulfanyl-dihydro-furan-2,5-dione (20 g, 91 mmol) was dissolved in CH$_2$Cl$_2$ (30 ml) and cooled to 0° C. Aluminum chloride (18.16 g, 136 mmol) was added and the mixture was stirred at room temperature for 1.5 hr. The reaction mixture was diluted with CH$_2$Cl$_2$ (1000 ml) and poured into ice-cooled conc HCl (1000 ml). The phases were separated and the aqueous phase was extracted with CH$_2$Cl$_2$(×3). The combined organic phases were washed with water, dried (MgSO$_4$) and evaporated to a brown solid. The solid was triturated with Et$_2$O to give 8.98 g of 4-oxo-thiochroman-2- carboxylic acid as a pale brown solid. $^1$H NMR (DMSO) δ 7.96 (1H, dd), 7.20-7.60 (3H, m), 4.40 (1H, dd), 3.20-3.33 (2H, m).

c) 6,11-Dihydro-5-thia-11-aza-benzo[α]fluorene-6-carboxylic acid ethyl ester

To a solution of 4-oxo-thiochroman-2-carboxylic acid (3 g, 14 mmol) and phenyl hydrazine (1.4 ml, 14 mmol) in EtOH (14 ml), H$_2$SO$_4$ (1.8 ml) was added, and the mixture was heated at reflux for 5 hr. The reaction was cooled to room temperature and the solid, which formed overnight, was filtered, washed with cold EtOH and cold Et$_2$O to give 2.26 g (51%) of 6,11-dihydro-5-thia-11-aza-benzo[α]fluorene-6-carboxylic acid ethyl ester as a crème solid. $^1$H NMR (CDCl$_3$) δ 8.47 (1H, br s), 7.53-7.58 (1H, m), 7.10-7.40 (7H, m), 5.00 (1H, s), 4.09 (2H, q), 1.15 (3H, t).

d) 6,11-Dihydro-5-thia-11-aza-benzo[α]fluorene-6-carboxylic acid

A solution of KOH (1.64 g, 29 mmol) in water (6 ml) was added to 6,11-dihydro-5-thia-11-aza-benzo[α]fluorene-6-carboxylic acid ethyl ester (2.26 g, 7 mmol) in EtOH (16 ml) and the mixture heated to reflux for 2 hr. The reaction mixture was acidified with 2N HCl and extracted with EtOAc. The organic phase was washed with brine, dried (MgSO$_4$) and evaporated to give 1.65 g (80%) of 6,11-dihydro-5-thia-11-aza-benzo[α]fluorene-6-carboxylic acid as a yellow foam. $^1$H NMR (DMSO) δ 12.55 (1H, br s), 11.70 (1H, s), 7.74-7.82 (1H, m), 7.00-7.57 (7H, m), 5.17 (1H, s).

e) 6,11-Dihydro-5-thia-11-aza-benzo[α]fluorene-6-carboxylic acid diethylamide

To 6,11-dihydro-5-thia-11-aza-benzo[α]fluorene-6-carboxylic acid (1.65 g, 6 mmol) in CH$_2$Cl$_2$ (15 ml) were added diethylamine (0.7 ml, 7 mmol), bromotripyrrolidinophosphonium hexafluorophosphate (2.75 g, 6 mmol) and diisopropylethylamine (3.1 ml, 18 mmol). The reaction was stirred at room temperature for 3 days. The reaction mixture was diluted with CH$_2$Cl$_2$ (100 ml), washed with 1N HCl, saturated NaHCO$_3$ soln, brine, dried (MgSO$_4$) and evaporated. The residue was purified by silica gel chromatography eluting with 50% EtOAc/petroleum ether to give 1.07 g (54%) of 6,11-dihydro-5-thia-11-aza-benzo[α]fluorene-6-carboxylic acid diethylamide as a yellow solid. $^1$H NMR (CDCl$_3$) δ 9.23 (1H, s), 7.33 (1H, dd), 7.20 (1H, dd), 7.69-7.08 (5H, m), 6.66-6.72 (1H, m), 5.33 (1H, s), 3.34-3.76 (4H, m), 1.39 (3H, t), 1.37 (3H, t).

Example 2

Synthesis of Chelate of Formula IIIa (Where G=C)

(Step a): Preparation of tris(methyloxycarbonylmethyl)methane 3-(methoxycarbonylmethylene)glutaric acid dimethylester (89 g, 267 mmol) in methanol (200 ml) was shaken with (10% palladium on charcoal: 50% water) (9 g) under an atmosphere of hydrogen gas (3.5 bar) for (30 h). The solution was filtered through kieselguhr and concentrated in vacuo to give 3-(methoxycarbonylmethyl)glutaric acid dimethylester as an oil, yield (84.9 g, 94%).
NMR $^1$H (CDCl$_3$), δ 2.48 (6H, d, J=8 Hz, 3×CH$_2$), 2.78 (1H, hextet, J=8 Hz CH$_2$) 3.7 (9H, s, 3×CH$_3$).

NMR $^{13}$C (CDCl$_3$), δ 28.6, CH; 37.50, 3×CH$_3$; 51.6, 3×CH$_2$; 172.28, 3×COO.

(Step b): Amidation of trimethylester with p-methoxy-benzylamine

Tris(methyloxycarbonylmethyl)methane [2 g, 8.4 mmol] was dissolved in p-methoxy-benzylamine (25 g, 178.6 mmol). The apparatus was set up for distillation and heated to 120° C. for 24 hrs under nitrogen flow. The progress of the reaction was monitored by the amount of methanol collected. The reaction mixture was cooled to ambient temperature and 30 ml of ethyl acetate was added, then the precipitated triamide product stirred for 30 min. The triamide was isolated by filtration and the filter cake washed several times with sufficient amounts of ethyl acetate to remove excess p-methoxy-benzylamine. After drying 4.6 g, 100%, of a white powder was obtained. The highly insoluble product was used directly in the next step without further purification or characterisation.

(Step c): Preparation of 1,1,1-tris[2-(p-methoxybenzylamino)ethyl]methane

To a 1000 ml 3-necked round bottomed flask cooled in a ice-water bath the triamide from step 2(a) (10 g, 17.89 mmol) was carefully added to 250 ml of 1M borane solution (3.5 g, 244.3 mmol) borane. After complete addition the ice-water bath was removed and the reaction mixture slowly heated to 60° C. The reaction mixture was stirred at 60° C. for 20 hrs. A sample of the reaction mixture (1 ml) was withdrawn, and mixed with 0.5 ml 5N HCl and left standing for 30 min. To the sample 0.5 ml of 50 NaOH was added, followed by 2 ml of water and the solution was stirred until all of the white precipitate dissolved. The solution was extracted with ether (5 ml) and evaporated. The residue was dissolved in acetonitrile at a concentration of 1 mg/ml and analysed by MS. If mono- and diamide (M+H/z=520 and 534) are seen in the MS spectrum, the reaction was not complete. To complete the reaction, a further 100 ml of 1M borane THF solution was added and the reaction mixture stirred for 6 more hrs at 60° C. and a new sample withdrawn following the previous sampling procedure. Further addition of the 1M borane in THF solution was continued as necessary until there was complete conversion to the triamine.

The reaction mixture was cooled to ambient temperature and 5N HCl is slowly added, [CARE: vigorous foam formation occurs!]. HCl was added until no more gas evolution was observed. The mixture was stirred for 30 min and then evaporated. The cake was suspended in aqueous NaOH solution (20-40%; 1:2 w/v) and stirred for 30 minutes. The mixture was then diluted with water (3 volumes). The mixture was then extracted with diethylether (2×150 ml) [CARE: do not use halogenated solvents]. The combined organic phases were then washed with water (1×200 ml), brine (150 ml) and dried over magnesium sulphate. Yield after evaporation: 7.6 g, 84% as oil.
NMR $^1$H (CDCl$_3$), δ: 1.45, (6H, m, 3×CH$_2$; 1.54, (1H, septet, CH); 2.60 (6H, t, 3×CH$_2$N); 3.68 (6H, s, ArCH$_2$); 3.78 (9H, s, 3×CH$_3$O); 6.94 (6H, d, 6×Ar). 7.20 (6H, d, 6×Ar).
NMR $^{13}$C (CDCl$_3$), δ: 32.17, CH; 34.44, CH$_2$; 47.00, CH$_2$; 53.56, ArCH$_2$; 55.25, CH$_3$O; 113.78, Ar; 129.29, Ar; 132.61; Ar; 158.60, Ar.

(Step d): Preparation of 1,1,1-tris(2-aminoethyl)methane 1,1,1-tris[2-(p-methoxybenzylamino)ethyl]methane (20.0 gram, 0.036 mol) was dissolved in methanol (100 ml) and Pd(OH)$_2$ (5.0 gram) was added. The mixture was hydrogenated (3 bar, 100° C., in an autoclave) and stirred for 5 hours. Pd(OH)$_2$ was added in two more portions (2×5 gram) after 10 and 15 hours respectively.

The reaction mixture was filtered and the filtrate was washed with methanol. The combined organic phase was evaporated and the residue was distilled under vacuum (1×10$^{-2}$, 110° C.) to give 2.60 gram (50%) of 1,1,1-tris(2-aminoethyl)methane.

NMR $^1$H (CDCl$_3$), δ 2.72 (6H, t, 3×CH$_2$N), 1.41 (H, septet, CH), 1.39 (6H, q, 3×CH$_2$).

NMR $^{13}$C (CDCl$_3$), δ 39.8 (CH$_2$NH$_2$), 38.2 (CH$_2$.), 31.0 (CH).

(Step e): Preparation of Formula IIIa (Where G=C)

To a solution of tris(2-aminoethyl)methane (4.047 g, 27.9 mmol) in dry ethanol (30 ml) was added potassium carbonate anhydrous (7.7 g, 55.8 mmol, 2 eq) at room temperature with vigorous stirring under a nitrogen atmosphere. A solution of 3-chloro-3-methyl-2-nitrosobutane (7.56 g, 55.8 mol, 2 eq) was dissolved in dry ethanol (100 ml) and 75 ml of this solution was dripped slowly into the reaction mixture. The reaction was followed by TLC on silica [plates run in dichloromethane, methanol, concentrated (0.88 sg) ammonia; 100/30/5 and the TLC plate developed by spraying with ninhydrin and heating]. The mono-, di- and tri-alkylated products were seen with RF's increasing in that order. Analytical HPLC was run using RPR reverse phase column in a gradient of 7.5-75% acetonitrile in 3% aqueous ammonia. The reaction was concentrated in vacuo to remove the ethanol and resuspended in water (110 ml). The aqueous slurry was extracted with ether (100 ml) to remove some of the trialkylated compound and lipophilic impurities leaving the mono and desired dialkylated product in the water layer. The aqueous solution was buffered with ammonium acetate (2 eq, 4.3 g, 55.8 mmol) to ensure good chromatography. The aqueous solution was stored at 4° C. overnight before purifying by automated preparative HPLC.

Yield (2.2 g, 6.4 mmol, 23%).

Mass spec; Positive ion 10 V cone voltage. Found: 344; calculated M+H=344.

NMR $^1$H (CDCl$_3$), δ 1.24 (6H, s, 2×CH$_3$), 1.3 (6H, s, 2×CH$_3$), 1.25-1.75 (7H, m, 3×CH$_2$, CH), (3H, s, 2×CH$_2$), 2.58 (4H, m, CH$_2$N), 2.88 (2H, t CH$_2$N$_2$), 5.0 (6H, s, NH$_2$, 2×NH, 2×OH).

NMR $^1$H ((CD$_3$)$_2$SO) δ1.1 4×CH; 1.29, 3×CH$_2$; 2.1 (4H, t, 2×CH$_2$);

NMR $^{13}$C ((CD$_3$)$_2$SO), δ 9.0 (4×CH$_3$), 25.8 (2×CH$_3$), 31.0 2×CH$_2$, 34.6 CH$_2$, 56.8 2×CH$_2$N, 160.3; C=N.

HPLC conditions: flow rate 8 ml/min using a 25 mm PRP column

A=3% ammonia solution (sp.gr=0.88)/water; B=Acetonitrile

| Time | % B |
|---|---|
| 0 | 7.5 |
| 15 | 75.0 |
| 20 | 75.0 |
| 22 | 7.5 |
| 30 | 7.5 |

Load 3 ml of aqueous solution per run, and collect in a time window of 12.5-13.5 min.

Example 3

Synthesis of Precursors of the Invention for $^{99m}$Tc Labelling

The chelate produced in Example 2 may be conjugated at R$^1$ or R$^2$ of a compound of Formula I via the bridgehead —CH$_2$CH$_2$NH$_2$ group of the chelate in order to form a precursor compound.

Example 4

$^{99m}$Tc Labelling of the Precursors of Example 3

For $^{99m}$Tc labelling, 50 □g of a precursor compound will be added to a nitrogen filled vial and dissolved in 50 □L water, 150 □L of sodium gluconate solution (25 mg in 6 mL H$_2$O), 100 □L ammonium acetate (pH 4.0, 50 mM), 1 mL TcO$_4$ soln (500 MBq) and 50 □L SnCl$_2$ soln (20 mg in 100 mL H$_2$O). The mixture will be heated at 75° C. for 20 minutes before analysis by ITLC and HPLC.

Example 5

Preparation of (±)-6,11-dihydro-5-thia-11-aza-benzo [α]fluorene-6-carboxylic acid N-1-[$^{18}$F]-propyl-N-propylamide [Compound 12]

(i) Preparation of (±)-6,11-dihydro-5-thia-11-aza-benzo[α]fluorene-6-carboxylic acid propylamide

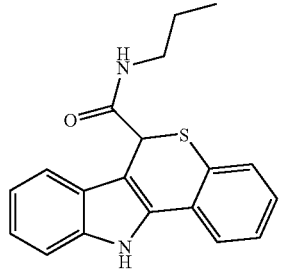 [SMILES: CCCNC(=O)C1Sc2ccccc2-c2[nH]c3ccccc3c21]

This compound can be made using the synthetic route described for the dipropylamide version (compound 12f of Okubo et al Bioorg. Med. Chem. 2004 12 3569-3580) replacing dipropylamine with a N-propyl-N-propyltosylate amine.

(ii) Preparation of (±)-6,11-dihydro-5-thia-11-aza-benzo[α]fluorene-6-carboxylic acid N-1-[$^{18}$F]-propyl-N-propylamide

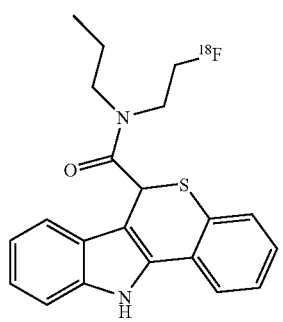 [SMILES: CCCN(CC[18F])C(=O)C1Sc2ccccc2-c2[nH]c3ccccc3c21]

To 5.1.4. (±)-6,11-dihydro-5-thia-11-aza-benzo[α]fluorene-6-carboxylic acid propylamide in a suitable solvent (acetonitrile, DMSO, DMF, THF, Dioxane) is added a base (LDA, NaH, or similar). To the mixture is added $^{18}$F fluoropropyl bromide (or other leaving group like tosylate etc) and the mixture is heated to 50-100° C. for 5-30 min, followed by HPLC purification. Protection of the indole amine is required during radioflorination.

Example 6

Preparation of (±)-6,11-dihydro-5-thia-11-aza-benzo[α]fluorene-6-[$^{11}$C]carboxylic acid dipropylamide

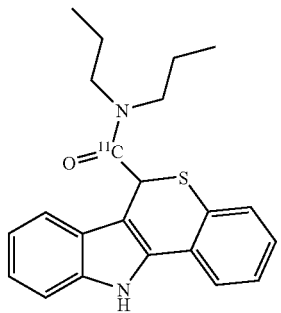 [SMILES: CCCN(CCC)[11C](=O)C1Sc2ccccc2-c2[nH]c3ccccc3c21]

6,11-dihydro-5-thia-11-aza-benzo[α]fluorene is deprotonated using a strong base, such as potassium carbonate, and the resultant deprotonated intermediate is reacted with 1 mM [$^{11}$C]CO$_2$ to produce 5.1.4. (±)-6,11-dihydro-5-thia-11-aza-benzo[α]fluorene-6-[$^{11}$C]-carboxylic acid. Reaction of this reagent with a coupling reagent [such as described by Christensen Molecules 2001; 6; pp 47-51] to produce an activated ester or mixed anhydride followed by addition of dipropylamine to provide the title compound.

Example 7

Preparation of 11-methyl-6,11-dihydro-5-thia-11-aza-benzo[α]fluorene-6-carboxylic acid diethylamide (non-radioactive Compound 3)

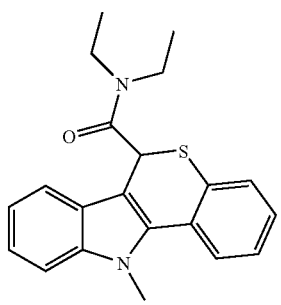 [SMILES: CCN(CC)C(=O)C1Sc2ccccc2-c2c1c1ccccc1n2C]

This method is an adaptation of "Method D" described by Okubo et al, supra.

100 mg (0.3 mmol) of 6,11-Dihydro-5-thia-11-aza-benzo[α]fluorene-6-carboxylic acid diethylamide (synthesis described in Example 1) was dissolved in 3 ml of DMSO. 84 mg (1.5 mmol) potassium hydroxide was added and the reaction mixture stirred at room temperature for 30 minutes. 0.04 ml (0.6 mmol) methyl iodide was added dropwise at room temperature and the reaction mixture was stirred for 1 hour. The reaction was quenched with 20 ml water, and extracted with 2×20 ml ether. The organic was dried (MgSO$_4$) and removed in vacuo. The residue was purified by column chromatography over silica using a 3:7 mixture of ethyl acetate and hexane as eluant. Appropriate fractions were combined and the solvent removed in vacuo to give the title compound as a yellow solid.

HPLC: 94.3%

500 MHz $^1$H-NMR (CDCl$_3$) δ (ppm): 1.10 (3H, m), 1.34 (3H, m), 3.39-3.70 (4H, m), 4.01 (3H, s), 5.14 (1H, s), 7.12-7.7.41 (7H, m), 7.72 (1H, d).

Example 8

Preparation of 11-isobutyl-6,11-dihydro-5-thia-11-aza-benzo[α]fluorene-6-carboxylic acid diethylamide (non-radioactive Compound 4)

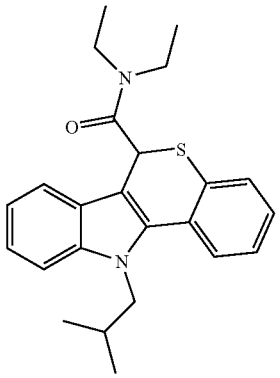 [SMILES: CCN(CC)C(=O)C1Sc2ccccc2-c2c1c1ccccc1n2CC(C)C]

The method of claim 9 was used but replacing methyl iodide with 1-bromo-2-methylpropane in order to obtain the isobutyl derivative. The product was obtained as a white solid.

HPLC 91.2%

500 MHz $^1$H-NMR (CDCl$_3$) δ (ppm): 0.76 (6H, dd), 1.10 (3H, m), 1.34 (3H, m), 2.16 (1H, m), 3.39-3.70 (4H, m), 4.24-4.38 (2H, m), 7.12-7.7.41 (7H, m), 7.72 (1H, d).

Example 9

Preparation of 11-isopropyl-6,11-dihydro-5-thia-11-aza-benzo[α]fluorene-6-carboxylic acid diethylamide (non-radioactive Compound 5)

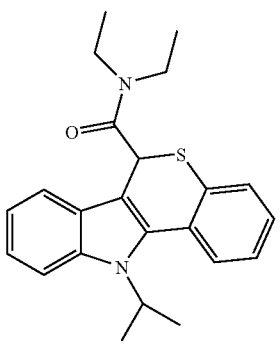 [SMILES: CCN(CC)C(=O)C1Sc2ccccc2-c2c1c1ccccc1n2C(C)C]

The method of claim 9 was used but replacing methyl iodide with 1-bromopropane in order to obtain the isopropyl derivative. The product was obtained as a white solid.

HPLC 90% Yield 44%

500 MHz $^1$H-NMR (CDCl$_3$) δ (ppm): 1.10 (3H, m), 1.34 (3H, m), 1.60 (3H, m), 1.88 (3H, m), 3.39-3.70 (4H, m), 5.07 (1H, s), 5.11 (1H, m), 7.10-7.60 (8H, m).

Example 10

Preparation of 11-prop-2-ynyl-6,11-dihydro-5-thia-11-aza-benzo[α]fluorene-6-carboxylic acid diethylamide (non-radioactive Compound 6/Compound 9P$^2$)

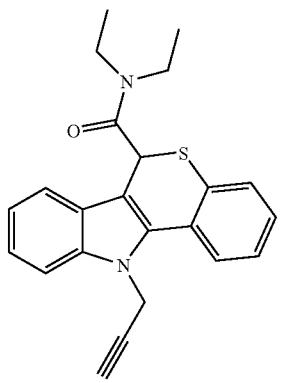 [SMILES: C#CCn1c2c(c3ccccc31)C(C(=O)N(CC)CC)Sc1ccccc1-2]

The method of claim 9 was used but replacing methyl iodide with propargyl bromide 80% in toluene in order to obtain the prop2ynyl derivative. The product was obtained as a yellow solid.

HPLC 99.3%

500 MHz $^1$H-NMR (CDCl$_3$) δ (ppm): 1.10 (3H, m), 1.34 (3H, m), 2.50 (1H, s), 3.39-3.70 (4H, m), 4.91-5.06 (2H, m), 5.20 (1H, s), 7.11-7.50 (7H, m), 7.89 (1H, d).

Example 11

Preparation of 11-(2-methyl-allyl)-6,11-dihydro-5-thia-11-aza-benzo[α]fluorene-6-carboxylic acid diethylamide (non-radioactive Compound 7)

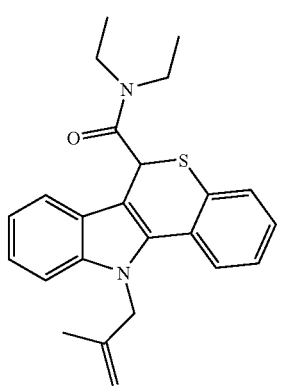 [SMILES: C=C(C)Cn1c2c(c3ccccc31)C(C(=O)N(CC)CC)Sc1ccccc1-2]

The method of claim 9 was used but replacing methyl iodide with 3-bromo-2-methylpropene in order to obtain the 2-methyl-allyl derivative. The product was obtained as a yellow solid.

HPLC 99.2% Yield 41%

500 MHz $^1$H-NMR (CDCl$_3$) δ (ppm): 1.10 (3H, m), 1.34 (3H, m), 1.91 (3H, s), 3.31-3.66 (4H, m), 4.61-4.82 (3H, m,), 5.08 (1H, s), 5.21 (1H, s), 7.12-7.53 (8H, m).

Example 12

Preparation of 11-(4-fluoro-butyl)-6,11-dihydro-5-thia-11-aza-benzo[α]fluorene-6-carboxylic acid diethylamide (non-radioactive Compound 8)

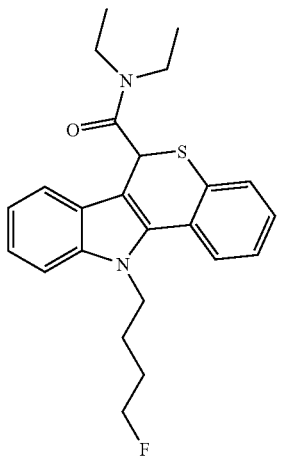 [SMILES: CCN(CC)C(=O)C1Sc2ccccc2-c2c1c1ccccc1n2CCCCF]

The method of claim 9 was used but replacing methyl iodide with bromofluorobutane in order to obtain the 4-fluoro-butyl derivative. The product was obtained as a yellow solid.

HPLC 96% Yield 33%

500 MHz $^1$H-NMR (CDCl$_3$) δ (ppm): 1.10 (3H, m), 1.34 (3H, m), 1.78 (2H, m), 2.08 (1H, m), 3.31-3.66 (4H, m), 4.40-4.50 (4H, m), 5.10 (1H, s), 7.11-7.50 (7H, m), 7.89 (1H, d).

Example 13

Preparation of 11-[1-(2-fluoro-ethyl)-1H-[1,2,3]triazol-4-ylmethyl]-6,11-dihydro-5-thia-11-aza-benzo[α]fluorene-6-carboxylic acid diethylamide (non-radioactive Compound 9)

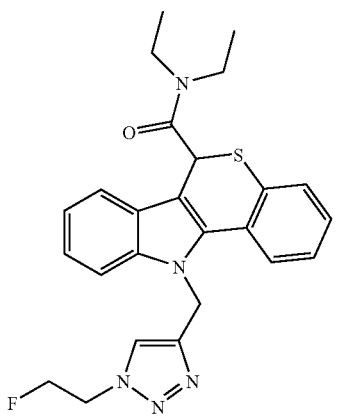 [SMILES: CCN(CC)C(=O)C1Sc2ccccc2-c2c1c1ccccc1n2Cc1cn(CCF)nn1]

1-Azido-2-fluoro ethane was synthesized by adding to a solution of fluoroethyltosylate (100 mg, 0.46 mmol) in anhydrous dimethylformamide 2 ml sodium azide (90 mg, 1.4 mmol) at room temperature under nitrogen. The mixture was stirred for 24 hours. The product was prepared as a solution in dimethylformamide after filtering off the solid. The solution was used without further purification to the next step.

To a solution of copper (II) sulfate pentahydrate (1.6 mg, 0.007 mmol) and L-ascorbic acid (2.5 mg, 0.014 mmol) in water 0.1 ml was added a solution of non-radioactive Compound 9P$^2$ as prepared in Example 10 (50 mg, 0.134 mmol) in anhydrous dimethylformamide 1 ml and a solution of 1-Azido-2-fluoro ethane in dimethylformamide (0.16 mmol) at room temperature under nitrogen. The reaction mixture was stirred at 90° C. for 10 hours. After cooling, the reaction was then quenched with 20 ml water, extracted with dichloromethane 2×20 ml. The organic was dried (MgSO$_4$) and removed in vacuo. The residue was purified by column chromatography over silica using a 3:7 mixture of ethyl acetate and hexane as eluant. Appropriate fractions were combined and the solvent was removed in vacuo to give the product as a yellow solid.

500 MHz $^1$H-NMR (CDCl$_3$) δ (ppm): 1.12 (3H, m), 1.40 (3H, m), 2.19 (2H, s), 3.38-3.60 (4H, m), 5.12 (1H, s), 5.45 (2H, m), 5.56 (2H, m), 7.12-7.28 (5H, m), 7.44 (3H, m).

MS: m/z=462 (M$^+$) found (calculated mass 462)

Example 14

Preparation of 11-(2-fluoro-ethyl)-6,11-dihydro-5-thia-11-aza-benzo[a]fluorene-6-carboxylic acid diethylamide [non-radioactive Compound 10]

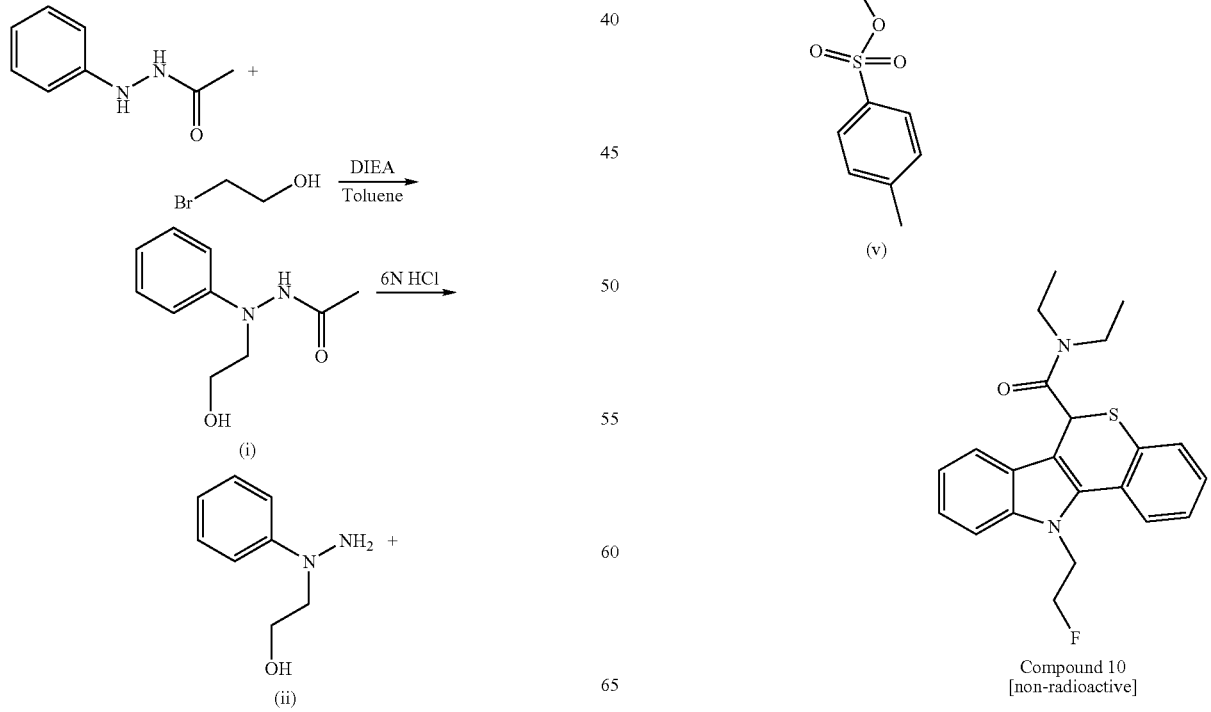

Synthesis of acetyl-2-(2-hydroxyethyl)-2-phenylhydrazine (i)

To a solution of 1-acetyl-2-phenylhydrazine (2 g, 13.3 mmol) in anhydrous toluene 20 ml was added bromoethanol (1.04 ml, 14.6 mmol), diisopropylethylamine (2.54 ml, 14.6 ml) at room temperature. The reaction mixture was refluxed under nitrogen for 40 hours. After cooling, the reaction was then quenched with 100 ml water, extracted with dichloromethane 2×100 ml. The organic was dried ($MgSO_4$) and removed in vacuo. The residue was purified by flash column chromatography over silica using a gradient 50% mixture of ethyl acetate and hexane to 100% ethyl acetate as eluant. Appropriate fractions were combined and the solvent was removed in vacuo to give the product as a yellow oil 0.9 g (Yield 35%).

GC/MS: m/z=194 ($M^+$).

Synthesis of 2-(N-phenyl-hydrazino)-ethanol (ii)

A solution of acetyl-2-(2-hydroxyethyl)-2-phenylhydrazine (i) (0.5 g, 2.57 mmol) in 6N hydrogen chloride 5 ml was refluxed for 2 hours. The reaction was cooled to room temperature and basified with 6N sodium hydroxide to PH 8. The solution was extracted with DCM 2×50 ml, washed with brine 2×30 ml. The organic was dried ($MgSO_4$) and removed in vacuo. The residue was used to next step without further purification.

GC/MS: m/z=152 ($M^+$).

Synthesis of 11-(2-Hydroxy-ethyl)-6,11-dihydro-5-thia-11-aza-benzo[α]fluorene-6-carboxylic acid diethylamide (iv)

To a solution of 2-(N-phenyl-hydrazino)-ethanol (ii) (0.59 g, 1.9 mmol) and 4-oxo-thiochroman-2-carboxylic acid diethylamide (iii) (0.5 g, 1.9 mmol) in ethanol 10 ml was added conc. sulfuric acid 0.5 ml. The reaction mixture was stirred and refluxed for 20 hours. It was then cooled to room temperature and poured onto water 50 ml. The resulting precipitate was collected by filtration and washed with water (3×30 ml). It was then dried in desiccators under vacuum with $P_2O_5$ as the drying agent to give the product 11-(2-Hydroxy-ethyl)-6,11-dihydro-5-thia-11-aza-benzo[α]fluorene-6-carboxylic acid diethylamide (iv) as a yellow solid 0.62 g, which was used to next step without further purification. Yield: 86%.

500 MHz $^1$H-NMR ($CDCl_3$) δ (ppm): 1.12 (3H, m), 1.40 (3H, m), 3.38-3.70 (4H, m), 4.05-4.15 (2H, m), 4.40 (1H, m), 4.60 (1H, m), 5.31 (1H, s), 7.12-7.47 (7H, m), 7.90 (1H, d).

Synthesis of 11-(2-Tosyloxy-ethyl)-6,11-dihydro-5-thia-11-aza-benzo[α]fluorene-6-carboxylic acid diethylamide (Compound 10P)

To a solution of 11-(2-Hydroxy-ethyl)-6,11-dihydro-5-thia-11-aza-benzo[α]fluorene-6-carboxylic acid diethylamide (iv) (100 mg, 0.26 mmol) in anhydrous dichloromethane 3 ml was added toluenesulfonyl chloride (100 mg, 0.52 mmol) and pyridine (0.2 ml, 2.6 mmol) at 0° C. under nitrogen. The reaction mixture was then stirred at room temperature for 48 hours. After quenched with 20 ml water, the mixture was extracted with dichloromethane 2×20 ml. The organic was dried ($MgSO_4$) and removed in vacuo. The residue was purified by flash column chromatography over silica using a gradient 20% mixture of ethyl acetate and hexane to 40% ethyl acetate as eluant. Appropriate fractions were combined and the solvent was removed in vacuo to give the product 11-(2-Tosyloxy-ethyl)-6,11-dihydro-5-thia-11-aza-benzo[α]fluorene-6-carboxylic acid diethylamide (Compound 10P) as a white solid 98 mg. Yield 48%.

500 MHz $^1$H-NMR ($CDCl_3$) δ (ppm): 1.12 (3H, m), 1.40 (3H, m), 2.12 (3H, s), 3.38-3.60 (4H, m), 4.40-4.71 (4H, m), 5.02 (1H, s), 7.12-7.27 (7H, m), 7.38 (1H, d), 7.42 (1H, d), 7.53 (1H, d), 7.75 (2H, d).

Synthesis of 11-(2-fluoroethyl)-6,11-dihydro-5-thia-11-aza-benzo[α]fluorene-6-carboxylic acid diethylamide (non-radioactive Compound 10)

To a solution of 11-(2-Tosyloxy-ethyl)-6,11-dihydro-5-thia-11-aza-benzo[α]fluorene-6-carboxylic acid diethylamide (Compound 10P) (100 mg, 0.19 mmol) in anhydrous acetonitrile 5 ml was added tetrabutylammonium fluoride 1.0 M in tetrahydrofuran (0.4 ml) at room temperature under nitrogen. The reaction was stirred for 3 hours. After quenched with 20 ml water, the mixture was extracted with dichloromethane 2×20 ml. The organic was dried ($MgSO_4$) and removed in vacuo. The residue was purified by flash column chromatography over silica using a gradient 20% mixture of ethyl acetate and hexane to 40% ethyl acetate as eluant. Appropriate fractions were combined and the solvent was removed in vacuo to give the product 11-(2-fluoroethyl)-6,11-dihydro-5-thia-11-aza-benzo[α]fluorene-6-carboxylic acid diethylamide (non-radioactive Compound 10) as a yellow solid 41 mg. Yield 55%.

500 MHz $^1$H-NMR ($CDCl_3$) δ (ppm): 1.12 (3H, m), 1.40 (3H, m), 3.38-3.60 (4H, m), 4.56-4.78 (2H, m), 4.85-4.98 (2H, m), 5.12 (1H, s), 7.12-7.48 (7H, m), 7.64 (1H, d).

MS: m/z 383 ($M^+$) found (calculated mass 383)

Example 15

Preparation of 11-(2-[$^{18}$F]Fluoroethyl)-6,11-dihydro-5-thia-11-aza benzo[α]fluorine-6-carboxylic acid diethylamide [Compound 10]

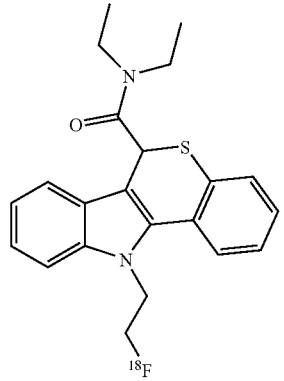 [SMILES: CCN(CC)C(=O)C1Sc2ccccc2-c2c1c1ccccc1n2CC[18F]]

Anhydrous potassium [$^{18}$F]fluoride was prepared by azeotropic drying of aqueous [$^{18}$F]fluoride in the presence of potassium carbonate (0.3 mg) and Kryptofix® 2.2.2. (1.8 mg) and anhydrous acetonitrile (3×0.5 ml). A solution of 11-(2-Tosyloxyethyl)-6,11-dihydro-5-thia-11-aza-benzo[α]fluorine-6-carboxylic acid diethylamide (1 mg; Compound 10P) in anhydrous DMSO (0.4 mL) was added to the vial containing anhydrous Potassium-Kryptofix® 2.2.2.[$^{18}$F]fluoride complex and the reaction vial sealed and heated to 130° C. with rapid stirring for 10 min. The resulting reaction mixture was cooled to room temperature, then diluted with 0.5 mL of HPLC mobile phase (acetonitrile:water, 60:40). An aliquot of the resulting solution was injected onto a analytical HPLC column (Phenomenex Luna 5u, C18(2) 100A 150 mm×4.6 mm) and eluted with a flow rate of 1 mL/min. The title compound was eluted from the column with a retention time of 8.5 minutes with a labelling yield of 50% by HPLC integration. The identity of the product was confirmed by co-elution with an authentic, unlabelled sample of 11-(2-Fluoroethyl)-6,11-dihydro-5-thia-11-aza-benzo[α]fluorine-6-carboxylic acid diethylamide.

Example 16

Preparation of 11-(2-methoxy-ethyl)-6,11-dihydro-5-thia-11-aza-benzo[α]fluorene-6-carboxylic acid diethylamide (non-radioactive Compound 11)

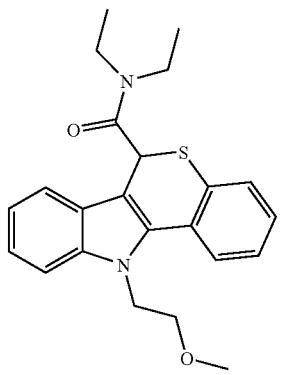 [SMILES: CCN(CC)C(=O)C1Sc2ccccc2-c2c1c1ccccc1n2CCOC]

To a stirred solution of intermediate iv (from the synthesis described in Example 15) (60 mg, 0.158 mmol) in anhydrous DMSO 3 ml was added potassium hydroxide (84 mg, 1.58 mmol) and iodomethane (1.58 mmol, 0.12 ml) at room temperature. The mixture was then stirred under nitrogen for 30 minutes. The reaction was poured onto water 50 ml, extracted with dichloromethane 2×20 ml, washed with brine 2×20 ml. The organic was dried (MgSO$_4$) and removed in vacuo. The residue was recrystallised from ethylacetate/hexane. The product was filtered and dried under vacuum to give a yellow solid 34 mg. Yield: 55%.

Example 17

Synthesis of 11-(2-[$^{11}$C]methoxy-ethyl)-6,11-dihydro-5-thia-11-aza-benzo[α]fluorine-6-carboxylic acid diethylamide [Compound 11]

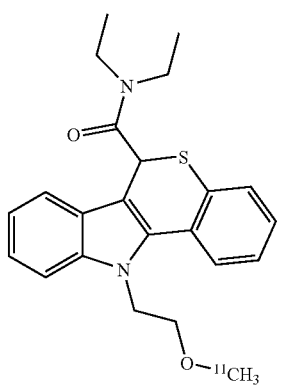 [SMILES: CCN(CC)C(=O)C1Sc2ccccc2-c2c1c1ccccc1n2CCO[11CH3]]

[$^{11}$C]Methyliodide is trapped in a stirred solution of 11-(2-hydroxy-ethyl)-6,11-dihydro-5-thia-11-aza-benzo[α]fluorine-6-carboxylic acid diethylamide (intermediate iv of Example 14) and a suitable base (e.g. potassium hydroxide, 10 equivalents) in anhydrous DMSO (0.4 mL). The reaction mixture is stirred rapidly at room temperature or elevated temperature to effect the [$^{11}$C]methylation reaction.

After consumption of the [$^{11}$C]methyliodide the reaction mixture is cooled to room temperature and purified by HPLC chromatography.

Example 18

Screening Method for Compounds of the Invention

The compounds were screened for their affinity for PBR using a method adapted from Le Fur et al 1983 [Life Sci. USA 33 pp 449-57].

The compounds to be tested [dissolved in 50 mM Tris-HCl, pH 7.4, 10 mM MgCl2 containing 1% DMSO] competed for binding to Wistar rat heart PBR to the receptor against 0.3 nM [$^3$H] PK-11195. The reaction was carried out in 50 mM Tris-HCl, pH 7.4 10 mM MgCl$_2$ for 15 minutes at 25° C.

$K_i$ values for the best compounds tested were found to be between 1.0 nM and 0.1 nM.

What is claimed is:
1. A compound of Formula I:

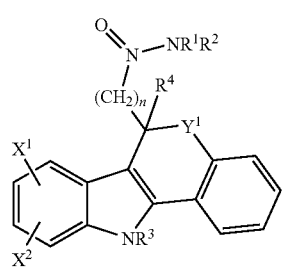

(I)

or a salt thereof, wherein said compound is labelled with an imaging moiety, and wherein:
X$^1$ and X$^2$ are independently selected from hydrogen, halogen, C$_{1-6}$ alkoxy, C$_{1-6}$ alkyl;
R$^1$ and R$^2$ are independently selected from C$_{1-6}$ alkyl, C$_{1-6}$ aminoalkyl, C$_{1-6}$ alkoxyalkyl, C$_{1-6}$ alkoxy, C$_{1-6}$ hydroxyalkyl, a polyethylene glycol (PEG) group, C$_{3-10}$ cycloalkyl, C$_{3-10}$ cycloethers, and C$_{3-10}$ cycloamines;
R$^3$ is C$_{1-6}$ [$^{18}$F]fluoroalkyl;
R$^4$ is hydrogen, C$_{1-6}$ alkyl, C$_{1-6}$ alkanoyl, C$_{1-6}$ cycloalkyl, C$_{1-6}$ fluoroalkyl, hydroxy, or halogen;
Y$^1$ is S, SO, SO$_2$, or CH$_2$; and,
n is 0 to 10.
2. The compound of claim 1 wherein:
X$^1$ and X$^2$ are both hydrogen;
R$^1$ and R$^2$ are independently selected from C$_{1-6}$ alkyl, C$_{1-6}$ methoxyalkyl or C$_{1-6}$ alkoxy;
R$^4$ is hydrogen, C$_{1-6}$ alkyl, C$_{1-6}$ alkanoyl, C$_{1-6}$ cycloalkyl or C$_{1-6}$ fluoroalkyl;
Y$^1$ is S, SO$_2$, or CH$_2$; and,
n is 0.
3. The compound of claim 2 wherein:
R$^1$ and R$^2$ are both C$_{1-6}$ alkyl;
R$^4$ is hydrogen, C$_{1-6}$ alkyl or C$_{1-6}$ alkanoyl; and,
Y$^1$ is S or SO$_2$.

4. The compound of claim 3 wherein:
R$^1$ and R$^2$ are both ethyl;
R$^4$ is hydrogen; and,
Y$^1$ is S.

5. A compound of Formula II:

(II)

or a salt thereof wherein:
R$^7$ is C$_{1-6}$ [$^{18}$F]fluoroalkyl; and,
Y$^2$ is S, SO, SO$_2$, or CH$_2$.

6. A method for the preparation of the compound of claim 1 comprising reaction of $^{18}$F-fluoride with a precursor of Formula Ia:

(Ia)

wherein:
X$^{11}$, X$^{12}$, R$^{14}$ and Y$^{11}$ are as defined for X$^1$, X$^2$, R$^4$ and Y$^1$, respectively, of Formula I of claim 1;
R$^{15}$ is the group —(CH$_2$)$_o$—C(=O)—NR$^{11}$R$^{12}$ wherein o is 0 to 10, and R$^{11}$ and R$^2$ are independently selected from C$_{1-6}$ alkyl, C$_{1-6}$ aminoalkyl, C$_{1-6}$ alkoxyalkyl, C$_{1-6}$ alkoxy, C$_{1-6}$ hydroxyalkyl, a polyethylene glycol (PEG) group, C$_{3-10}$ cycloalkyl, C$_{3-10}$ cycloethers, and C$_{3-10}$ cycloamines;
R$^{16}$ is hydrogen, and
R$^{13}$ is selected from an alkyl bromide, alkyl mesylate or alkyl tosylate.

7. A precursor for of Formula Ia (Ia)

wherein:
X$^{11}$ and X$^{12}$ are independently selected from hydrogen, halogen, C$_{1-6}$ alkoxy, C$_{1-6}$ alkyl;
R$^{14}$ is hydrogen, C$_{1-6}$ alkyl, C$_{1-6}$ alkanoyl, C$_{1-6}$ cycloalkyl, C$_{1-6}$ fluoroalkyl, hydroxy, or halogen;
Y$^{11}$ is S, SO, SO$_2$, or CH$_2$
R$^{15}$ is the group —(CH$_2$)$_o$—C(=O)—NR$^{11}$R$^{12}$ wherein o is 0 to 10, and R$^{11}$ and R$^2$ are independently selected from C$_{1-6}$ alkyl, C$_{1-6}$ aminoalkyl, C$_{1-6}$ alkoxyalkyl, C$_{1-6}$ alkoxy, C$_{1-6}$ hydroxyalkyl, a polyethylene glycol (PEG) group, C$_{3-10}$ cycloalkyl, C$_{3-10}$ cycloethers, and C$_{3-10}$ cycloamines; and,
R$^{16}$ is hydrogen, and
R$^{13}$ is selected from an alkyl bromide, alkyl mesylate or alkyl tosylate.

8. A pharmaceutical composition which comprises the compound of claim 1, together with a biocompatible carrier in a form suitable for mammalian administration.

9. A pharmaceutical composition which is a therapeutic composition comprising the compound of claim 5 together with a biocompatible carrier in a form suitable for mammalian administration.

10. A kit comprising a precursor of Formula Ia (Ia)

wherein:
X$^{11}$ and X$^{12}$ are independently selected from hydrogen, halogen, C$_{1-6}$ alkoxy, C$_{1-6}$ alkyl;
R$^{14}$ is hydrogen, C$_{1-6}$ alkyl, C$_{1-6}$ alkanoyl, C$_{1-6}$ cycloalkyl, C$_{1-6}$ fluoroalkyl, hydroxy, or halogen;
Y$^{11}$ is S, SO, SO$_2$, or CH$_2$;
R$^{15}$ is the group —(CH$_2$)$_o$—C(=O)—NR$^{11}$R$^{12}$ wherein o is 0 to 10, and R$^{11}$ and R$^2$ are independently selected from C$_{1-6}$ alkyl, C$_{1-6}$ aminoalkyl, C$_{1-6}$ alkoxyalkyl, C$_{1-6}$ alkoxy, C$_{1-6}$ hydroxyalkyl, a polyethylene glycol (PEG) group, C$_{3-10}$ cycloalkyl, C$_{3-10}$ cycloethers, and C$_{3-10}$ cycloamines;
R$^{16}$ is hydrogen, and
R$^{13}$ is selected from an alkyl bromide, alkyl mesylate or alkyl tosylate.

11. A method for the in vivo diagnosis or imaging of a peripheral benzodiazepine (PBR) condition in a subject, comprising administration of a pharmaceutical composition comprising a compound of claim 1, and detecting uptake of said compound using an in vivo imaging method, wherein said PBR condition is selected from Parkinson's disease, multiple sclerosis, Alzheimer's disease, Huntington's disease, neuropathic pain, arthritis, asthma, atherosclerosis and cancer.

\* \* \* \* \*